(12) United States Patent
Jarrell et al.

(10) Patent No.: US 7,485,423 B2
(45) Date of Patent: Feb. 3, 2009

(54) LADDER ASSEMBLY AND SYSTEM FOR GENERATING DIVERSITY

(75) Inventors: Kevin Jarrell, Lincoln, MA (US); Jonah Keegan, New York, NY (US); Nathan Tichovolsky, Malden, MA (US); Bob Rogers, Arlington, MA (US)

(73) Assignee: Modular Genetics, Inc., Cambridge, MA (US)

( * ) Notice: Subject to any disclaimer, the term of this patent is extended or adjusted under 35 U.S.C. 154(b) by 155 days.

(21) Appl. No.: 11/271,562

(22) Filed: Nov. 11, 2005

(65) Prior Publication Data

US 2006/0223081 A1    Oct. 5, 2006

Related U.S. Application Data

(60) Provisional application No. 60/697,307, filed on Jul. 6, 2005, provisional application No. 60/626,589, filed on Nov. 11, 2004.

(51) Int. Cl.
*C12Q 1/68* (2006.01)
*C12P 19/34* (2006.01)

(52) U.S. Cl. ............................ 435/6; 435/91.1; 435/91.2

(58) Field of Classification Search ........................ None
See application file for complete search history.

(56) References Cited

U.S. PATENT DOCUMENTS

| | | | |
|---|---|---|---|
| 6,143,527 A | 11/2000 | Pachuk et al. | |
| 6,171,820 B1 | 1/2001 | Short | 435/69.1 |
| 6,939,689 B2 | 9/2005 | Short et al. | 435/69.1 |
| 6,946,296 B2 | 9/2005 | Patten et al. | 435/440 |
| 6,972,183 B1 | 12/2005 | Lafferty et al. | 435/7.4 |
| 6,979,733 B2 | 12/2005 | Zhao et al. | 536/23.2 |
| 6,995,017 B1 | 2/2006 | Stemmer | 435/440 |
| 7,018,793 B1 | 3/2006 | Short | 435/6 |
| 7,024,312 B1 | 4/2006 | Selifonov et al. | 702/19 |
| 7,078,035 B2 | 7/2006 | Short et al. | |
| 7,078,504 B2 | 7/2006 | Short et al. | |
| 7,105,297 B2 | 9/2006 | Minshull et al. | |
| 7,148,054 B2 | 12/2006 | Del Cardayre et al. | |
| 7,232,672 B2 | 6/2007 | Weiner et al. | 435/189 |
| 7,232,677 B2 | 6/2007 | Short et al. | 435/196 |
| 7,314,613 B2 | 1/2008 | Patten et al. | |
| 7,318,918 B2 | 1/2008 | Patten et al. | |
| 2004/0161752 A1 | 8/2004 | Jarrell et al. | |
| 2005/0129059 A1 | 6/2005 | Jiang et al. | |
| 2005/0186622 A1 | 8/2005 | Stemmer et al. | |
| 2005/0191688 A1 | 9/2005 | Selifonov et al. | |
| 2005/0266465 A1 | 12/2005 | Williams et al. | |
| 2006/0008844 A1 | 1/2006 | Stemmer et al. | |
| 2006/0045888 A1 | 3/2006 | Punnonen et al. | |
| 2006/0047611 A1 | 3/2006 | Selifonov et al. | |
| 2006/0051795 A1 | 3/2006 | Crameri et al. | |
| 2006/0084091 A1 | 4/2006 | Patten et al. | |
| 2006/0166225 A1 | 7/2006 | Patten et al. | |
| 2006/0177831 A1 | 8/2006 | Stemmer et al. | |
| 2006/0205003 A1 | 9/2006 | Gustafsson et al. | |
| 2006/0223143 A1 | 10/2006 | Patten et al. | |
| 2006/0234299 A1 | 10/2006 | Stemmer et al. | |
| 2006/0257890 A1 | 11/2006 | Minshull et al. | |
| 2006/0259995 A1 | 11/2006 | Cayouette et al. | |
| 2006/0275804 A1 | 12/2006 | Short et al. | |
| 2006/0286603 A1 | 12/2006 | Kolkman et al. | |
| 2007/0020235 A1 | 1/2007 | Patten et al. | |
| 2007/0020734 A1 | 1/2007 | Patten et al. | |
| 2007/0025966 A1 | 2/2007 | Patten et al. | |
| 2007/0026446 A1 | 2/2007 | del Cardayre et al. | |
| 2007/0031878 A1 | 2/2007 | Patten et al. | |
| 2007/0031943 A1 | 2/2007 | Jarrell et al. | |
| 2007/0048775 A1 | 3/2007 | Cardayre et al. | |
| 2007/0054313 A1 | 3/2007 | Crameri et al. | |
| 2007/0056053 A1 | 3/2007 | Gray et al. | |
| 2007/0065407 A1 | 3/2007 | Patten et al. | |

(Continued)

FOREIGN PATENT DOCUMENTS

EP        01644394        3/2005

(Continued)

OTHER PUBLICATIONS

Abelian, A., et al., "Targeting The A Site RNA Of The Escherichia Coli Ribosomal 30 S Subunit by 2'-O-Methyl Oligoribonucleotides: A Quantitative Equilibrium Dialysis Binding Assay And Differential Effects Of Aminoglycoside Antibiotics.", *Biochem. Journal* 383(2): 201-208, 2004.

(Continued)

*Primary Examiner*—Kenneth R. Horlick
*Assistant Examiner*—David C Thomas
(74) *Attorney, Agent, or Firm*—Margo H. Furman; Choate, Hall & Stewart LLP

(57) ABSTRACT

The present invention provides novel methods of generating a nucleic acid molecule. In certain embodiments, a double stranded nucleic acid chunk is generated from a ladder complex comprising partially complementary oligonucleotides, which chunk is combined with a nucleic acid acceptor molecule. In certain embodiments, the assembled chunk/nucleic acid acceptor molecule complex may be propagated in vivo or in vitro. The present invention also provides improved systems for generating a plurality of nucleic acid molecules that differ at one or more nucleotide positions. In certain embodiments, the plurality of nucleic acid molecules encodes a polypeptide or portion of a polypeptide.

27 Claims, 8 Drawing Sheets

U.S. PATENT DOCUMENTS

| | | | |
|---|---|---|---|
| 2007/0065838 | A1 | 3/2007 | Crameri et al. |
| 2007/0087373 | A1 | 4/2007 | Punnonen et al. |
| 2007/0087374 | A1 | 4/2007 | Punnonen et al. |
| 2007/0092887 | A1 | 4/2007 | Stemmer et al. |
| 2007/0274950 | A1 | 11/2007 | Patten et al. |
| 2007/0292954 | A1 | 12/2007 | Elledge |
| 2008/0031853 | A1 | 2/2008 | Patten et al. |
| 2008/0032378 | A1 | 2/2008 | Callen et al. |
| 2008/0047037 | A1 | 2/2008 | Callen et al. |
| 2008/0076710 | A1 | 3/2008 | Patten et al. |

FOREIGN PATENT DOCUMENTS

| | | |
|---|---|---|
| EP | 01528067 | 5/2005 |
| EP | 01555316 | 7/2005 |
| EP | 1565 205 | 8/2005 |
| EP | 1576 108 | 9/2005 |
| EP | 1201 768 | 12/2005 |
| EP | 01108058 | 2/2006 |
| EP | 01690868 A1 | 8/2006 |
| EP | 01696025 A2 | 8/2006 |
| EP | 01696025 A3 | 9/2006 |
| EP | 01707641 A2 | 10/2006 |
| EP | 0839185 B1 | 11/2006 |
| EP | 01717322 A2 | 11/2006 |
| EP | 01707641 A3 | 12/2006 |
| EP | 01717322 | 1/2007 |
| JP | 2005/245453 | 9/2005 |
| JP | 2007244399 | 9/2007 |
| JP | 2007252382 | 10/2007 |
| WO | WO-00/40715 A3 | 7/2000 |
| WO | WO-03/085094 A2 | 10/2003 |
| WO | WO 2005/093099 | 10/2005 |
| WO | WO 2005/093101 | 10/2005 |
| WO | WO 2005/097992 | 10/2005 |
| WO | 2005113592 | 12/2005 |
| WO | WO 2005/113592 | 12/2005 |
| WO | WO 2005/118853 | 12/2005 |
| WO | WO 2006/009888 | 1/2006 |
| WO | WO 2006/028684 | 3/2006 |
| WO | WO-2006/028684 A2 | 3/2006 |
| WO | WO-2006/083276 A2 | 8/2006 |
| WO | WO-2006/096527 A2 | 9/2006 |
| WO | WO-2006/099207 A2 | 9/2006 |
| WO | WO-2006/101584 A2 | 9/2006 |
| WO | WO-2006/127040 A2 | 11/2006 |
| WO | WO 2007/044083 | 4/2007 |
| WO | WO-2007044083 | 4/2007 |
| WO | WO-2007/124065 | 11/2007 |

OTHER PUBLICATIONS

Kierzek, E., et al., "The Influence Of Locked Nucleic Acid Residues On The Thermodynamic Properties Of 2'-O-Methyl RNA/RNA Heteroduplexes.", *Nucleic Acid Research* 33(16): 5082-5093, 2005.

Sandbrink, J., et al., "Investigation Of Potential RNA Bulge Stabilizing Elements.", *J Mol Recognit* 18(4): 318-326, 2005.

Suzuki, Y., et al., "A Novel High-Throughput (HTP) Cloning Strategy For Site-Directed Designed Chimeragenesis And Mutation Using The Gateway Cloning System.", *Nucleic Acid Research* 33(12): e109 (1-6), 2005.

Wright, A., et al., "Diverse Plasmid DNA Vectors By Directed Molecular Evolution Of Cytomegalovirus Promoters.", *Human Gene Therapy* 16(7): 881-892, 2005.

Doyle, "High-throughput Cloning For Proteomics Research," *Methods Mol. Biol.*, 310: 107-113, 2005.

Li, et al., "Ligation Independent Cloning Irrespective Of Restriction Site Compatibility," *Nucl. Acids Res.*, 25(20): 4165-4166, 1997.

Nisson, "Rapid And Efficient Cloning Of Alu-PCR Products Using Uracil DNA Glycosylase," *PCR Methods Appl.*, 1(2): 120-123, 1991.

Patten, et al., "Applications Of DNA Shuffling To Pharmaceuticals And Vaccines," *Curr Opin Biotechnol.*, 8(6): 724-733, 1997.

Silverman, et al., "Multivalent Avimer Proteins Evolved By Exon Shuffling Of A Family Of Human Receptor Domains," *Nature Biotech.*, 23:1556-1561, 2005.

Demarest et al., "Engineering stability into *Escherichia coli* secreted Fabs leads to increased functional expression", *Protein Eng Des Sel*, 19(7): 325-336, 2006.

Silverman et al., "Multivalent avimer proteins evolved byexon shuffling of a family of human receptor domains", *Nature Biotechnology*, 23(12): 1556-1561, 2005.

Donahue et al., "Rapid gene cloning using terminator primers and modular vectors", *Nucleic Acids Research*, 30(18): e95(1-6), 2002.

International Search Report, PCT/US2005/040748, published May 18, 2006.

Stemmer et al., "Single-step assembly of a gene and entire plasmid from large numbers of oligodeoxyribonucleotides", Gene, 164: 49-53, 1995.

Li et al., "Harnessing homologous recombination in vitro to generate recombinant DNA via SLIC", Nature Methods, 4 (3): 251-256, 2007.

Wu et al., "Simplified gene synthesis: A one-step approach to PCR-based gene construction", Journal of Biotechnology, 124: 496-503, 2006.

Kodumal et al., "Total synthesis of long DNA sequences: Synthesis of a contiguous 32-kb polyketide synthase gene cluster", PNAS, 101(44): 15573-15578, 2004.

Li, et al., *Applied Microbio. And Biotech.*, 75(3): 703-709, 2007.

Li, et al., *Nature Methods YNat. Methods*, 4(3): 251-256, 2007.

Barnes, *PNAS*, 91: 2216-2220, 1994.

Bolivar, et al., *Gene*, 2: 75-93, 1977.

Cadwell, et al., *PCR Methods Appl.*, 2: 28-33, 1992.

Chen, et al., *J. Am. Chem. Soc.*, 11: 8799-8800, 1994.

Crameri, et al., *BioTechniques*, 18: 194-196, 1995.

Dillon, et al., *BioTechniques*, 9: 298-300, 1990.

Goeddel, et al., *PNAS*, 76: 106-110, 1979.

Hayashi, et al., *BioTechniques*, 17: 310-314, 1994.

Heyneker, et al., *Nature*, 263: 748-752, 1976.

Hermes, et al., *Gene*, 84: 143-151, 1989.

Itakura, et al., *Science*, 198: 1056-1063, 1977.

Lashkari, et al., *PNAS*, 92: 7912-7915, 1995.

Mandecki, et al., *Gene*, 68: 101-107, 1988.

Mandecki, et al., *Gene*, 94: 103-107, 1992.

Prodromou, et al., *Protein Eng.*, 5: 827-829, 1992.

Stemmer, *Nature*, 370: 389-391, 1994.

Stemmer, *PNAS*, 91: 10747-10751, 1994.

Watson, *Gene*, 70: 399-403, 1988.

Zhu, *Biotechniques*, 43: 356-359, 2007.

Alienberg, et al., "Description of a PCR-based technique for DNA splicing and mutagenesis by producing 5' overhangs with run through stop DNA synthesis utilizing Ara-C", BMC Biotechnology, Biomed Central LTD., 5(1):23-28, 2005.

Ailenberg, et al., "Site-directed mutagenesis using a PCR-based staggered re-annealing method without restriction enzymes", Biotechniques, 22(4):624-630, 1997.

Coljee, et al., "Seamless gene engineering using RNA- and DNA-overhang cloning", Nature Biotechnology, 18:789-791, 2000.

Donahue, et al., "Rapid gene cloning using terminator primers and modular vectors", Nucleic Acids Research, 30(18):E95, 2002.

Gap Amplification

Circular Template

Linear Template

Generating Diversity in a Seamless Ladder

Alternative Oligos

Pooled

Individual

Generating Diversity in a Gapped Ladder

Alternative Oligos

Pooled

Individual

Multiple Areas of Diversity in a Seamless Ladder

Alternative Oligos

Pooled

Individual

Diversity Amplification

Contiguous Insertion

Discrete Insertion

Diversity Amplification

Contiguous Insertion

Discrete Insertion

LADDER ASSEMBLY AND SYSTEM FOR GENERATING DIVERSITY

CROSS-REFERENCE TO RELATED APPLICATIONS

This application claims priority to U.S. Provisional Patent Application No. 60/697,307 filed Jul. 6, 2005, and to U.S. Provisional Patent Application No. 60/626,589 filed Nov. 11, 2004, each of which is incorporated herein by reference in its entirety. This application is also related to co-pending U.S. patent application Ser. No. 11/132,356, filed May 18, 2005, which is a continuation of co-pending U.S. patent application Ser. No. 09/897,712, filed Jun. 29, 2001, which is a continuation-in-part of U.S. patent application Ser. No. 09/225,990, filed Jan. 5, 1999, now U.S. Pat. No. 6,358,712, each of which is incorporated herein by reference in its entirety. This application is also related to co-pending U.S. patent application Ser. No. 10/383,135, filed Mar. 5, 2003, which is a continuation-in-part of co-pending U.S. patent application Ser. No. 09/910,354, filed Jul. 20, 2001, each of which is incorporated herein by reference in its entirety.

BACKGROUND OF THE INVENTION

Molecular Biology provides powerful tools for engineering and recombination of nucleic acids. Restriction enzymes, site-directed mutagenesis, various polymerase-chain-reaction (PCR)-based strategies, synthesis-based strategies, homologous recombination, and other approaches, are all employed in the production of engineered nucleic acids and/or the variation of nucleic acid sequences. New techniques, or improved versions of existing techniques, continue to be developed. However, further room for improvement exists.

A variety of techniques have been developed for generating diversity in or among nucleic acid sequences. Some such techniques involve recombination between or among related nucleic acid sequences, typically followed by selection of desired recombined sequences (for example, see Patten et al., U.S. Pat. Nos. 6,579,678 and 6,613,514). Such approaches have significant drawbacks, however, not the least of which is that due to the stochastic nature of recombination, the practitioner must rely on a chance recombination event to generate a particular nucleic acid sequence. Furthermore, one or more of the parental molecules may fail to undergo recombination or may be reconstituted in a recombination reaction, such that extensive screening is required to identify new recombinants of interest.

Hence, there is still a need for improved methods of generating engineered nucleic acid sequences and of generating diversity in a population of nucleic acid molecules.

SUMMARY OF THE INVENTION

In some embodiments, the present invention provides systems for producing engineered nucleic acids that allow complete control over the sequence. These inventive systems are particularly useful for the production of sets of nucleic acid molecules, and allow complete control over the sequence of every nucleic acid in the set. In some embodiments, the inventive system produces related sets of nucleic acid molecules, whose sequences are substantially identical to one another and differ only at pre-determined locations and in pre-determined ways. In certain embodiments, nucleic acid molecules of the related set encode polypeptides or portions of polypeptides.

In certain embodiments, the inventive systems involve production of nucleic acid "chunks" that can be linked to one another. Each "chunk" is generated through assembly of an oligonucleotide ladder. Chunks may be amplified and/or linked with nucleic acid acceptor molecules, and may be propagated in vitro or in vivo.

In certain embodiments, an oligonucleotide ladder is created by annealing complementary overlapping oligonucleotides to one another. The oligonucleotide ladder may contain one or more gaps between the individual oligonucleotides that comprise one strand of the ladder such that certain portions of one or more oligonucleotides of the oligonucleotide ladder do not hybridize to a complementary oligonucleotide. In some embodiments, multiple versions of the oligonucleotide ladder that differ at one or more positions are assembled by providing alternate versions of one or more oligonucleotides that differ at one or more nucleotide positions. These multiple versions of the oligonucleotide ladder may be assembled by annealing individual alternate versions of one or more oligonucleotides in separate reactions. Additionally or alternatively, the multiple versions of the oligonucleotide ladder may be assembled in a single annealing reaction by providing the individual alternate versions of one or more oligonucleotides in a pooled reaction.

In certain embodiments of the present invention, two primers are provided and the oligonucleotide ladder is extended with these primers in a polymerase-mediated extension reaction to create a double stranded chunk. According to teachings of the present invention, prior ligation of the annealed oligonucleotides of the oligonucleotide ladder is not necessary for the polymerase-mediated extension reaction of the primers to occur. Furthermore according to teachings of the present invention, the presence of one or more gaps in one or both strands that comprise the oligonucleotide ladder does not prevent the polymerase-mediated extension reaction. In some embodiments of the present invention, at least one of the primers used in the polymerase-mediated extension of the ladder complex contains a terminator nucleotide that does not serve as a replication template for the polymerase used in the extension reaction under at least one set of reaction conditions, such that the generated double stranded nucleic acid molecule will contain at least one overhang. In one aspect of this embodiment, the terminator nucleotide may be copied by a different polymerase and/or the same polymerase under a different set of reaction conditions. In some embodiments, at least one of the primers used in the polymerase-mediated extension of the ladder complex contains a terminator structure that does not serve as a replication template for the polymerase used in the extension reaction.

In certain embodiments of the present invention, the oligonucleotide ladder contains a sequence that encodes a polypeptide containing a functional domain or a portion of a functional domain of a protein of interest. According to teachings of the present invention, the oligonucleotide ladder can be engineered to contain one or more point mutations, deletions, insertions or rearrangements such that the functional domain or portion of the functional domain of the polypeptide it encodes is altered. One of ordinary skill in the art will be able to choose the particular point mutations, deletions, insertions or rearrangements to be introduced, if any, based on his or her experimental, commercial or other needs. In certain embodiments, the present invention can be used to perform a saturation mutagenesis of one or more amino acids of the given polypeptide.

In some embodiments, the present invention can be used to introduce one or more homologous domains from one or more homologous polypeptides. For example, one or more homologous domains of two or more homologous polypeptides can be "swapped" to determine whether a chimeric polypeptide containing one or more swapped homologous domains has an improved or novel function or property. Additionally or alternatively, in certain embodiments, the present invention provides a fast and efficient method to "swap" a domain of interest in a given polypeptide with one or more homologous domains from one or more otherwise non-homologous polypeptides.

In certain embodiments, the present invention can be used to introduce sequence variation in a non-coding nucleic acid molecule. For example, methods of the present invention can be used to introduce or alter a regulatory element that regulates a nucleic acid of interest that encodes a polypeptide. In some embodiments, a promoter region or element can be introduced or altered according to certain methods of the present invention to determine which nucleic acid residues of the promoter region or element are important for directing expression of a polypeptide under control of that promoter or element. In some embodiments, methods of the present invention can be used to introduce an otherwise heterologous promoter element into a promoter region, for example, a tissue specific or inducible control element. In some embodiments, methods of the present invention can be used to introduce an intron or splicing site into a nucleic acid of interest that encodes a polypeptide, or alter an existing intron or splicing site. In some embodiments, methods of the present invention can be used to introduce a regulatory element into the 3' or 5' untranslated region ("UTR") of a particular mRNA molecule, or alter an existing 3' or 5' UTR regulatory element. Numerous other possible elements are known in the art and one of ordinary skill in the art will be able to choose which regulatory elements to alter and how to alter them according to teachings of the present invention.

BRIEF DESCRIPTION OF THE DRAWING

FIG. 1 shows two embodiments of Ladder Assembly and Chunk Generation. In FIGS. 1A and 1B, primers 1 and 2 anneal to the single stranded regions of oligos 1 and 6, respectively. The asterisks in primers 1 and 2 indicate a terminator that does not serve as a replication template for at least one polymerase. The terminator may be either a terminator nucleotide or a terminator structure. Amplifying the annealed ladder via a polymerase-mediated extension reaction using a polymerase that will not replicate the terminator(s) of the primer(s) results in a chunk that contains at least one 5' overhang beginning at the position of the terminator(s) in the primer(s). FIGS. 1A and 1B shows a ladder composed of six oligonucleotides, but any number of oligonucleotides may be annealed to form the ladder according to the present invention.

FIG. 2 shows two embodiments of Gap Amplification. Two primers are designed such that amplifying a template nucleic acid molecule by extending the primers in a polymerase-mediated extension reaction results in a nucleic acid acceptor molecule.

FIG. 6 shows a seamless ladder composed of six oligonucleotides, but any number of oligonucleotides may be annealed to form the ladder according to the present invention. For the sake of simplicity, FIG. 6 shows a seamless oligonucleotide ladder, according to the present invention, the oligonucleotide ladder may contain one or more gaps between adjacent oligonucleotides comprising one strand of the ladder complex. The multiple oligonucleotide variants may be annealed in a pooled reaction (FIG. 6B). Alternatively, the multiple oligonucleotide variants may be annealed in individual reactions (FIG. 6C).

FIG. 7 shows two embodiments of Diversity Amplification, wherein multiple chunks are inserted into a nucleic acid acceptor molecule.

FIG. 8 shows two embodiments of Diversity Amplification, wherein multiple chunks are inserted into a nucleic acid acceptor molecule to generate a related set of nucleic acid molecules.

DEFINITIONS

Figure 1A:
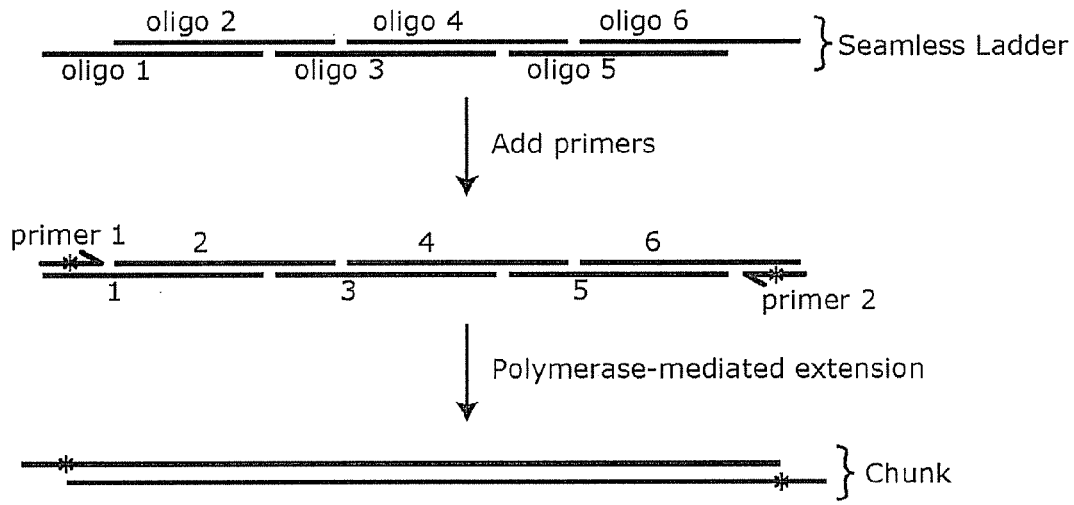
FIG. 1A shows an example of seamless ladder assembly wherein no gaps are left between adjacent oligonucleotides that anneal to a common binding partner oligonucleotide.

"Binding partner oligonucleotide": The term "binding partner oligonucleotide" as used herein refers to an oligonucleotide that is complementary to and may be annealed to at least one other oligonucleotide of the ladder complex. A binding partner oligonucleotide may be a "Bridging Oligonucleotide" or a "Terminal Oligonucleotide" as defined herein. Each bridging oligonucleotide of a ladder complex (see definition of "Ladder Complex", infra) anneals to at least two binding partner oligonucleotides. Each terminal oligonucleotide (see definition of "Terminal Oligonucleotide", infra) of the ladder complex anneals to at least one binding partner oligonucleotide.

"Bridging oligonucleotide": The term "bridging oligonucleotide" as used herein refers to an oligonucleotide that is complementary to and may be annealed to at least two other binding partner oligonucleotides of a ladder complex. The at least two complementary binding partner oligonucleotides may anneal to the bridging oligonucleotide seamlessly such that there are no nucleotides of the bridging oligonucleotide positioned between the two binding partner oligonucleotide that are not hybridized to the two complementary oligonucleotides. Alternatively, the two complementary oligonucleotides that anneal to the bridging oligonucleotide may anneal such that a gap is created between them (see definition of "Gap", infra).

"Bubble": The term "bubble" as used herein refers to a portion of a double stranded nucleic acid molecule that contains one or more adjacent nucleotides on one strand that are not complementary to their cognate (see definition of "Cognate", infra) nucleotides present in the opposite strand. These mis-matched nucleotide pairs thus do not hybridize with each other, resulting in a "bubble" in the double stranded nucleic acid molecule.

"Chunk", "Chunk molecule": The terms "chunk" and "chunk molecule" as used herein refer to a double stranded nucleic acid molecule that is generated from a ladder complex according to any method of the present invention. In certain embodiments, a chunk may be generated by annealing oligonucleotides to form a ladder complex and amplifying the ladder complex by polymerase-mediated extension of primers that anneal to the ladder complex. According to this embodiment, the nucleic acid strands that comprise the chunk are continuous, as opposed to the "Nicked" or "Gapped" strands that comprise the ladder complex. In certain embodiments, the chunk is combined with a nucleic acid acceptor molecule (see definition of "Nucleic Acid Acceptor Molecule", infra) in a process termed "Chunk Insertion". In certain embodiments, the chunk includes at least one overhang that is at least partly complementary to at least one overhang of the nucleic acid acceptor molecule. According to teachings of this invention, the overhang(s) may be generated, for example, by employing primers that contain one or more terminator oligonucleotides that are not copied by the polymerase used in the extension. The chunk may be linked to the nucleic acid acceptor molecule by any of several methods known to one of ordinary skill in the art, including but not limited to, ligation, ligation-independent cloning and amplification.

"Cognate": The term "cognate" as used herein refers to two nucleotides on opposite strands of a double stranded nucleic acid molecule, which two nucleotides are positioned such that if the nucleotides were complementary (e.g., adenine and thymine, or guanine and cytidine) they would hybridize with each other. As used herein, two nucleotides may be cognate even if they are not complementary, so long as they are positioned such that if they were complementary, they would hybridize.

"Diversity Amplification": The term "diversity amplification" as used herein refers to the insertion of chunks into a nucleic acid acceptor molecule (see definition of "Nucleic Acid Acceptor Molecule", infra). In certain embodiments, two or more alternate versions of at least one chunk are provided such that, after insertion, the resulting double stranded nucleic acid molecules contain different alternate versions of the chunk. For example, if two chunks are inserted into a nucleic acid acceptor molecule and each chunk is provided in two alternate versions, there will be four alternate versions of product molecules produced. The number of alternate product molecules will increase as a function of the number of chunk insertion sites and the number of alternate chunk versions. Exponential amplification can occur as different combinations of chunk and chunk versions are employed. In certain embodiments, the two or more chunks are inserted into a nucleic acid acceptor molecule at contiguous locations such that the multiple chunks are directly adjacent to each other in the resulting double stranded nucleic acid molecule. Additionally or alternatively, in some embodiments, the two or more chunks are inserted at discrete locations in the nucleic acid acceptor molecule such that the multiple chunks are not directly adjacent to each other in the resulting double stranded nucleic acid molecule. The two or more chunks may be inserted into the nucleic acid acceptor molecule simultaneously or sequentially.

"Gap": The term "gap" as used herein refers to a space between two oligonucleotides that anneal to a complementary bridging oligonucleotide in the oligonucleotide ladder (see definition of "Ladder", infra). For example, when a bridging oligonucleotide anneals to two binding partner oligonucleotides such that there is at least one nucleotide on the bridging oligonucleotide that is situated between the two binding partner oligonucleotides and has no cognate nucleotide on either binding partner, a gap is created between the two binding partner oligonucleotides. The length of the gap is determined by the number of nucleotides on the bridging oligonucleotide positioned between the two binding partner oligonucleotides that have no cognate nucleotides on either binding partner oligonucleotide. Thus, if only a single nucleotide of the bridging oligonucleotide situated between the two binding partner oligonucleotides has no cognate nucleotide on either binding partner oligonucleotide, the gap between the binding partner oligonucleotides is one nucleotide in length. The region of the bridging oligonucleotide that is situated at the gap (i.e., the region between the two binding partner oligonucleotides) is necessarily single stranded. The presence of a gap between two oligonucleotides of a nucleic acid strand necessarily results in the nucleic acid strand being "nicked" (see definition of "Nicked", infra).

"Gap Amplification": The term "gap amplification" as used herein refers to a process of preparing a nucleic acid acceptor molecule for insertion of a chunk. Gap amplification comprises subjecting a template nucleic acid molecule to one or more polymerase-mediated extensions such that one or more linear nucleic acid acceptor molecules are generated (see definition of "Nucleic Acid Acceptor Molecule", infra). Gap amplification may be performed on a circular template nucleic acid molecule (for example, see FIG. 2A). Alternatively, gap amplification may be performed on a linear template nucleic acid molecule (for example, see FIG. 2B). In certain embodiments, gap amplification is performed according to any method disclosed in U.S. Pat. No. 6,358,712, incorporated herein by reference. In some embodiments, gap amplification is performed according to any method disclosed in U.S. patent application Ser. No. 10/383,135, incorporated herein by reference.

"Ladder", "Oligonucleotide ladder", "Ladder complex": The terms "ladder", "oligonucleotide ladder" and "ladder complex" as used herein refer to a nucleic acid molecule that is generated by annealing overlapping, partially complementary oligonucleotides and is at least partly double stranded over a portion of its length. In certain embodiments, the ladder complex comprises at least first and second oligonucleotides, wherein at least a portion of the first oligonucleotide is at least partly complementary to at least a portion of the second oligonucleotide. In some embodiments, the ladder complex comprises at least first, second and third oligonucleotides, wherein the first and second oligonucleotides are complementary to each other over at least a portion of their lengths, and wherein the third oligonucleotide is at least partly complementary to at least a portion of the second oligonucleotide that is different from the portion of the second oligonucleotide that is complementary to the first oligonucleotide. In some embodiments, each strand of the ladder complex comprises at least two adjacent oligonucleotides that are not covalently linked to one another but are held in association with one another by virtue of complementarity with an oligonucleotide of the other strand. Thus, each strand of the ladder complex is nicked (see definition of "Nicked", infra) at one or more places along its length. According to certain of these embodiments, each strand of the ladder contains a single terminal oligonucleotide (see definition of "Terminal Oligonucleotide", infra) at one end of each strand and one or more bridging oligonucleotides. Furthermore, according to certain of these embodiments, each ladder complex may contain two terminal oligonucleotides, which terminal oligonucleotides are positioned on separate strands at opposite ends of the ladder complex. The two terminal oligonucleotides are maintained in association with each other by means of hybridization of the partially complementary bridging oligonucleotides of the ladder complex (for example, see FIG. 1).

"Nicked": The term "nicked" as used herein refers to a nucleic acid strand that is not continuous. For instance, a nucleotide strand composed of two or more oligonucleotides wherein at least two of the oligonucleotides that comprise that strand are not covalently linked to each other is a nicked strand. In certain embodiments, the nicked nucleic acid strand is generated by annealing a collection of oligonucleotides to form a ladder complex such that some members of the collection form one nicked strand while other members of the collection form a complementary nicked strand to which the first strand is annealed. A nick may span 1, 2, 3, 4, 5, 6, 7, 8, 9, 10, 15, 20, 25 or more nucleotides in length. Alternatively, the nick may span 0 nucleotides in length. For example, when a bridging oligonucleotide anneals to two binding partner oligonucleotides such that there is no nucleotide on the bridging oligonucleotide between the two binding partner oligonucleotides that is not annealed to either binding partner, the two binding partner oligonucleotides comprise a nicked strand, which nick is 0 nucleotides in length.

"Nucleic acid acceptor molecule": The term "nucleic acid acceptor molecule" as used herein refers to a nucleic acid molecule that is capable of being combined with a chunk. In certain embodiments, the nucleic acid acceptor molecule comprises a linearized vector that has been manipulated such that it is capable of being combined with a chunk. In some embodiments, the nucleic acid acceptor molecule includes at least one overhang that is at least partly complementary to at least one overhang of the chunk molecule. In certain embodiments, the overhang is generated by polymerase-mediated extension of two primers. In some aspects of these embodiments, at least one of the primers used in the polymerase-mediated extension contains a terminator nucleotide that does not serve as a replication template for the polymerase used. The nucleic acid acceptor molecule may be linked to the chunk by any of several methods known to one of ordinary skill in the art, including but not limited to, ligation, ligation-independent cloning and amplification. A single nucleic acid acceptor molecule may be linked to more than one chunk.

"Primer": The term "primer", as used herein, refers to an oligonucleotide that is characterized by an ability to be extended against a template nucleic acid strand, so that a polynucleotide strand whose sequence is complementary to that of at least a portion of the template strand, is produced linked to the primer. Primers may be of any convenient length selected by the practitioner so long as they are able to anneal to and be extended against a template nucleic acid molecule. For example, the primers of the present invention may be 5, 6, 7, 8, 9, 10, 11, 12, 13, 14, 15, 16, 17, 18, 19, 20, 25, 30, 35, 40, 45, 50 or more nucleotides in length. In certain embodiments, one or more primers that are extended against a template nucleic acid strand contain one or more nucleotides or structures, referred to as "Terminator Nucleotides" or "Terminator Structures" (see definitions, infra), that cannot be copied by the polymerase used in the extension reaction under the conditions of the reaction. In certain embodiments, one or more terminator nucleotides present in the primer can be copied by a different polymerase and/or the same polymerase under different extension conditions.

"Related Set of Nucleic Acid Molecules": According to the present invention, a set of nucleic acid molecules whose sequences are substantially identical to one another and differ only at pre-determined locations and in pre-determined ways constitutes a "related set of nucleic acid molecules". In certain embodiments, individual sequences within a set are, for example, at least 50, 55, 60, 65, 70, 75, 80, 85 or 90 percent identical to one another. In other embodiments, individual sequences within a set are, for example, at least 91, 92, 93, 94, 95, 96, 97, 98, or 99 percent identical to one another. In many embodiments, individual sequences will contain regions of perfect identity interdispersed with one or more regions of variability. In some embodiments, different members of a related set will share one or more consensus sequences. Such consensus sequences can define the set. In some embodiments, such consensus sequences can alternatively or additionally be associated with particular functional attributes of the sequences (e.g., can encode or represent a protein motif, such as a binding of catalytic motif, of particular activity.) In some embodiments of the invention, members of a related set of nucleic acid molecules will contain protein-coding sequence. In certain such embodiments, different members of the related set will differ from each other in that, at one or more pre-determined positions, a different amino acid is encoded; in some embodiments the related set, when taken together, includes sequences encoding every possible amino acid at a given position.

"Saturation mutagenesis": The term "saturation mutagenesis" as used herein refers to a method of generating a comprehensive set of alterations at one or more positions in a given nucleic acid of polypeptide sequence. For example, saturation mutagenesis of a single position in a nucleic acid sequence will generally produce four nucleic acid molecules, each of which contains one of adenine, cytidine, guanine and thymine at the selected nucleotide position. In some embodiments, different numbers of mutants can be generated, for example, through the use of non-natural nucleotides. "Saturation mutagenesis" of a single position in an amino acid sequence will produce twenty different polypeptides (more if non-natural amino acids are employed). It will be understood that saturation mutagenesis of a given position in a polypeptide is generally accomplished through production of a related set of nucleic acid molecules encoding every possible amino acid at the selected position. It will be further understood that more than one position in a particular nucleic acid or polypeptide sequence may be subjected to saturation mutagenesis.

"Substantially similar": As used herein, the term "substantially similar", as applied to nucleic acid sequences, refers to two or more nucleic acid molecules or portions of nucleic acid molecules, which nucleic acid molecules or portions contain one or more identical nucleotides positioned at the same relative location along the nucleic acid molecule or portion. In certain embodiments, the term substantially similar refers to nucleic acid molecules or portions of nucleic acid molecules whose nucleotide sequences are, for example, 50, 55, 60, 65, 70, 75, 80, 85 or 90 percent identical over a given length of the nucleic acid molecule or portion. In other embodiments, the term substantially similar refers to nucleic acid molecules or portions of nucleic acid molecules whose nucleotide sequences are, for example, 91, 92, 93, 94, 95, 96, 97, 98, or 99 percent identical over a given length of the nucleic acid molecule or portion. The length of the nucleic acid molecule or portion over which two or more nucleic acid molecules or portions are substantially similar may be, for example, 10, 15, 20, 25, 30, 35, 40, 45, 50, 60, 70, 80, 90, 100, 200, 300, 400, 500, 600, 700, 800, 900, 1000 or more nucleotides. In some embodiments, two nucleic acid molecules or portions of nucleic acid molecules are substantially similar if they are able to hybridize to the same portion of another nucleic acid molecule under stringent hybridization conditions. As will be clear from the context, the term "substantially similar", as applied to polypeptide sequences, alternately refers to two or more polypeptides or portions of polypeptides, which polypeptides or portions contain one or more of identical or similar amino acids positioned at the same relative location along the polypeptide or portion. It is known in the art which amino acids are similar to each other. For example, amino acid with aliphatic side chains, including glycine, alanine, valine, leucine, and isoleucine, are similar; amino acids having aliphatic-hydroxyl side chains, including serine and threonine, are similar; amino acids having amide-containing side chains, including asparagine and glutamine, are similar; amino acids having aromatic side chains, including phenylalanine, tyrosine, and tryptophan, are similar; amino acids having basic side chains, including lysine, arginine, and histidine, are similar; and amino acids having sulfur-containing side chains, including cysteine and methionine, are similar. In certain embodiments, the term substantially similar refers to polypeptides or portions of polypeptides whose amino acid sequences are, for example, 50, 55, 60, 65, 70, 75, 80, 85 or 90 percent identical or similar over a given length of the polypeptide or portion. In other embodiments, the term substantially similar refers to polypeptides or portions of nucleic acid molecules whose amino acid sequences are, for example, 91, 92, 93, 94, 95, 96, 97, 98, or 99 percent identical or similar over a given length of the polypeptide or portion. The length of the polypeptide or portion over which two or more polypeptides or portions are substantially similar may be, for example, 5, 6, 7, 8, 9, 10, 15, 20, 25, 30, 35, 40, 45, 50, 60, 70, 80, 90, 100, 200, 300, 400, 500, 600, 700, 800, 900, 1000 or more amino acids.

"Terminal oligonucleotide": The term "terminal oligonucleotide" as used herein refers to an oligonucleotide that is positioned at one end of one strand of an annealed oligonucleotide ladder. In certain embodiments, each ladder complex of the present invention contains two terminal oligonucleotides, each terminal oligonucleotide being positioned at opposite ends of the ladder complex on opposite strands. In certain embodiments, the terminal oligonucleotide anneals to only one other oligonucleotide of the ladder complex (either a bridging oligonucleotide or the other terminal oligonucleotide). In some embodiments, the terminal oligonucleotide may anneal to more than one oligonucleotide of the ladder complex. In certain embodiments, the terminal oligonucleotide contains a single stranded overhang that is not annealed to another oligonucleotide of the ladder complex.

"Terminator": As will be clear from the context, the term "terminator" as used herein may refer to either a terminator nucleotide or a terminator structure (see definitions of "Terminator Nucleotide" and "Terminator Structure", infra), which terminator nucleotide or terminator structure is not capable of being copied by at least one polymerase in a polymerization reaction.

"Terminator Nucleotide", "Terminator Residue": The terms "terminator nucleotide" and "terminator residue" as used herein refer to a nucleotide or nucleotide analog that is not capable of being copied by at least one polymerase in a polymerization reaction under at least one set of conditions. A given terminator nucleotide may be capable of being copied by a different polymerase under otherwise identical or similar conditions. Additionally or alternatively, a given terminator nucleotide may be capable of being copied by the same polymerase under a different set of polymerization conditions. In certain embodiments, the terminator nucleotide is contained in a primer that is used in a polymerase-mediated extension reaction. Furthermore, a primer containing a terminator nucleotide may be used in conjunction with any method disclosed in U.S. Pat. No. 6,358,712 or in U.S. patent application Ser. No. 10/383,135, each of which is incorporated herein by reference. As but one non-limiting example, the primer may contain one or more ribonucleotide residues that are not copied by at least one polymerase used in the polymerase-mediated extension reaction. As another non-limiting example, the primer may contain one or more 2'-O-methyl residues that are not copied by at least one polymerase used in the polymerase-mediated extension reaction.

"Terminator Structure": The term "terminator structure" as used herein refers to a structural feature of nucleic acid molecule, at a position in relation to the phosphate backbone where a nucleotide is normally located, that does not permit a polymerase used in a polymerization reaction to move beyond that structural feature and copy nucleotides beyond the structure feature. Any physical moiety that functions to stop the polymerase from copying nucleotides beyond a given position along the nucleic acid strand is a terminator structure. Additionally, the absence of a nucleotide residue at a given position along the phosphate backbone (i.e., an "abasic site") may be a terminator structure if it functions to stop the polymerase from copying nucleotides beyond that abasic site. In certain embodiments, the terminator structure is contained in a primer. As used herein, the term structural feature does not refer to a nucleotide or a nucleotide analog (see definition of "Terminator Nucleotide", supra).

DETAILED DESCRIPTION OF CERTAIN EMBODIMENTS

The present invention provides novel systems for generating engineered nucleic acid molecules. In certain embodiments, a double stranded nucleic acid chunk is generated from a ladder complex comprising partially complementary oligonucleotides, which chunk can be linked with a nucleic acid acceptor molecule. In some embodiments, the assembled chunk/nucleic acid acceptor molecule complex may be propagated in vivo or in vitro. The present invention also provides improved systems for generating a related set of nucleic acid molecules that differ at one or more pre-determined locations. In certain embodiments, the nucleic acid molecules of the related set encode polypeptides or polypeptide portions.

Additional and alternative embodiments of the invention are discussed in detail below. Those of ordinary skill in the art will understand, however, that various modifications to these embodiments are within the scope of the appended claims. It is the claims and equivalents thereof that define the scope of the present invention, which is not and should not be limited to or by this description of certain embodiments.

Ladder Assembly

The present invention provides systems for generating engineered nucleic acid molecules, wherein the nucleic acid molecule sequence is predetermined and chosen by the practitioner. In certain embodiments, a ladder complex is generated by annealing two or more oligonucleotides, wherein at least a portion of each oligonucleotide is at least partly complementary to at least a portion of at least one other oligonucleotide of the ladder complex. In some embodiments, at least a first and a second oligonucleotide are provided, wherein at least a portion of the first oligonucleotide is at least partly complementary to at least a portion of the second oligonucleotide. According to these embodiments, the first and second oligonucleotides are annealed to form a ladder complex. In some embodiments, at least a first, second and third oligonucleotide are provided, wherein the first and second oligonucleotides are at least partly complementary to each other over at least a portion of their lengths, and wherein the third oligonucleotide is at least partly complementary to a portion of the second oligonucleotide that is different from the portion of the second oligonucleotide that is complementary to the first oligonucleotide. The first, second and third oligonucleotides are annealed to form a ladder complex. According to these embodiments, one strand of the ladder complex comprises the first and the third oligonucleotides and is therefore nicked, while the other strand is not nicked since it comprises only the second oligonucleotide.

In certain embodiments, a collection of partially complementary oligonucleotides is provided comprising a first terminal oligonucleotide, a second terminal oligonucleotide and at least two bridging oligonucleotides. These oligonucleotides are annealed to form a ladder complex. According to these embodiments, each strand of the ladder complex comprises at least one terminal oligonucleotide and at least one bridging oligonucleotide and is thus nicked in at least one place along its length. The first and second terminal oligonucleotides are positioned in separate strands and are located at opposite ends of the ladder complex. The first and second terminal oligonucleotides are non-covalently connected to each other through the partially complementary bridging oligonucleotides. Since the sequence of the individual oligonucleotides comprising the ladder complex is determined by the practitioner, method according to these embodiments allow for the production of a ladder complex comprising any sequence.

The oligonucleotides used to form the ladder complex may be produced by any method. In some embodiments, synthetic oligonucleotides may be produced according to any one of several techniques that are known in the art. In some embodiments, the oligonucleotides may be produced enzymatically by a DNA polymerase that copies a template nucleic acid molecule to produce a single stranded product oligonucleotide. According to these embodiments, the enzymatically produced oligonucleotide may be separated and purified from the template nucleic acid molecule and the polymerase before annealing to form the ladder complex. In certain embodiments, the oligonucleotides are generated by the dissociation of double stranded nucleic acid molecules and subsequent isolation of the single strands. The various oligonucleotides used to form the ladder complex need not be produced by the same methods. One of ordinary skill in the art will be able to choose the particular method of generating oligonucleotides based on his or her experimental, commercial or other needs.

In accordance with teachings of the present invention, the sequences of the oligonucleotides used to form the ladder complex are predetermined and may consist of any sequence chosen by the practitioner. However, practicalities of hybridization and polymerization dictate that certain constraints on nucleotide sequence be kept in mind when designing or choosing the oligonucleotides to be used. For example, since each oligonucleotide used to form the ladder complex must anneal with at least one other oligonucleotide of the ladder complex, the practitioner should preferably choose and/or design oligonucleotides that have minimal or no self-complementarity if possible. One of ordinary skill in the art will be aware of other constraints that must be accommodated when designing or choosing oligonucleotides to be used in accordance with the present invention based on his or her experimental, commercial or other needs.

The length of the oligonucleotides used to form the ladder complex may be of any convenient length, so long as they anneal to form a ladder complex. Thus, the oligonucleotides may be, for example, 2, 3, 4, 5, 6, 7, 8, 9, 10, 15, 20, 25, 30, 35, 40, 45, 50, 55, 60, 65, 70, 75, 80, 85, 90, 95, 100 or more nucleotides in length. In certain embodiments, the oligonucleotides used to form the ladder complex are all the same length. In some embodiments, two or more oligonucleotides used to form the ladder complex are of different lengths. The practitioner may choose the length of the oligonucleotide based on his or her experimental, commercial or other needs.

Similarly, the number of nucleotides over which complementary oligonucleotides of the ladder complex hybridize may be of any convenient number, so long as the strength of the hybridization is enough to keep the ladder complex from dissociating. Thus, the number of nucleotides over which complementary oligonucleotides of the ladder complex hybridize may be, for example, 2, 3, 4, 5, 6, 7, 8, 9, 10, 15, 20, 25, 30, 35, 40, 45, 50, 55, 60, 65, 70, 75, 80, 85, 90, 95, 100 or more nucleotides in length. In certain embodiments, the number of nucleotides over which complementary oligonucleotides of the ladder complex hybridize is the same for each pair of complementary oligonucleotides. In other embodiments, the number of nucleotides over which complementary oligonucleotides of the ladder complex hybridize is different for different pairs of complementary oligonucleotides. Furthermore, a bridging oligonucleotide of the ladder complex that hybridizes with two binding partner oligonucleotides (either two bridging oligonucleotides or one bridging oligonucleotide and one terminal oligonucleotide) need not hybridize with its two binding partner oligonucleotides over the same number of nucleotides. The practitioner may choose the number of nucleotides over which complementary oligonucleotides of the ladder complex hybridize based on his or her experimental, commercial or other needs.

In certain embodiments, the oligonucleotides of the ladder complex may be annealed simultaneously in one reaction. Additionally or alternatively, the individual oligonucleotides may be annealed to the growing ladder complex sequentially, such that the ladder complex is assembled one oligonucleotide at a time. One of ordinary skill in the art will be able to determine the appropriate conditions that permit to annealing. For example, one of ordinary skill in the art will be able to determine the appropriate temperature at which to anneal the oligonucleotides based on the nucleotide composition or length of the oligonucleotides he or she has selected. Similarly, one of ordinary skill in the art will be able to determine whether to anneal the oligonucleotides in the presence of various salts or other components that may facilitate annealing and/or may reduce non-specific or intramolecular interactions. After generation of the ladder complex, excess unannealed oligonucleotides may be separated and/or removed from the ladder complex by any of several known techniques in the art including, but not limited to, size fractionation, precipitation, exonuclease digestion of unannealed oligonucleotides or non-denaturing gel electrophoresis.

Seamless Ladder Assembly

In some embodiments of the present invention, at least one strand of the ladder complex comprises two or more oligonucleotides that are directly adjacent to each other, leaving no gap between them. According to these embodiments, in a ladder complex comprising a first terminal oligonucleotide, a second terminal oligonucleotide and at least two bridging oligonucleotides, each bridging oligonucleotide of the ladder complex anneals to two other binding partner oligonucleotides of the ladder complex (either two other bridging oligonucleotides or one terminal oligonucleotide and one bridging oligonucleotide) and each nucleotide of the bridging oligonucleotide is cognate to a nucleotide of one of the two binding partner oligonucleotides. Hence, in this ladder complex, the only oligonucleotides that may optionally contain nucleotides that are not cognate to nucleotides of another oligonucleotide of the ladder complex are the two terminal oligonucleotides which anneal to only one bridging oligonucleotide, and may thus comprise single stranded overhangs at the end of the ladder complex. A seamless ladder is thus a double stranded nucleic acid molecule whose individual strands are nicked in at least one position, and that optionally contains one or more single stranded overhangs at either end. One embodiment of seamless ladder assembly is depicted in FIG. 1A.

In some embodiments, the seamless ladder complex comprises two strands that are perfectly complementary to each other over the region that they anneal. According to these embodiments, there are no mis-matched cognate nucleotide pairs and no bubbles are present within the ladder complex. In some embodiments, the two strands of the ladder complex contain one or more cognate nucleotide pairs that are mis-matched, resulting in one or more bubbles in the ladder complex. If the ladder complex is subjected to a polymerase-mediated extension reaction to form a chunk (see Chunk Generation section, infra), two separate chunks will be generated, one chunk comprising a sequence containing the mis-matched nucleotide(s) present in one strand of the ladder complex and a second chunk comprising a sequence containing the mis-matched nucleotide(s) present in the other strand of the ladder complex. Methods of the present invention apply equally to seamless ladders that either do or do not contain bubbles formed by cognate nucleotides that are mis-matched.

Gapped Ladder Assembly

Figure 1B:
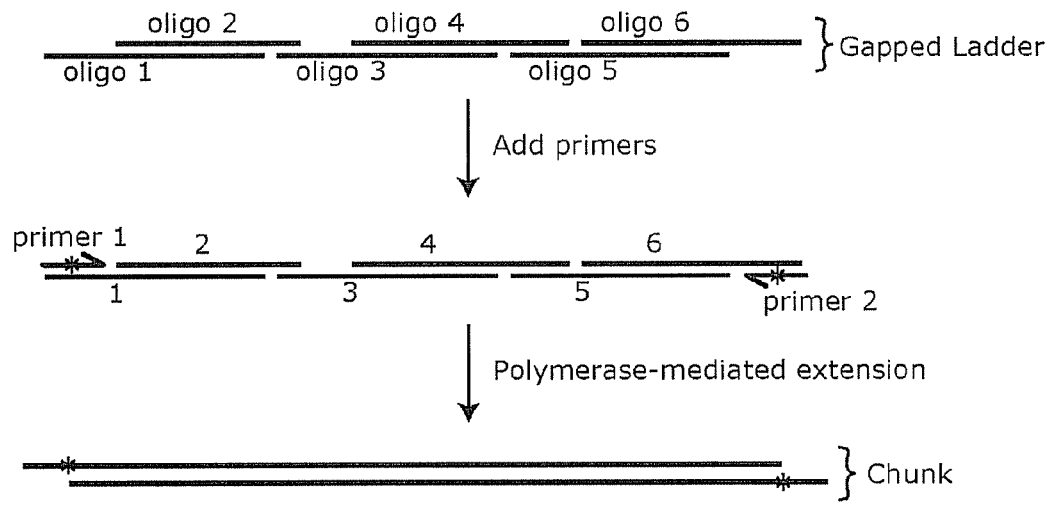
FIG. 1B shows an example of gapped ladder assembly wherein a gap between oligo 2 and oligo 4 is created when they anneal to oligo 3.

In certain embodiments of the present invention, at least one strand of the ladder complex comprises at least two oligonucleotides that are not directly adjacent to each other, leaving a gap between them. According to these embodiments, in a ladder complex comprising a first terminal oligonucleotide, a second terminal oligonucleotide and at least two bridging oligonucleotides, each bridging oligonucleotide of the ladder complex anneals to two other binding partner oligonucleotides (either two other bridging oligonucleotides or one terminal oligonucleotide and one bridging oligonucleotide) and at least one nucleotide of at least one bridging oligonucleotide has no cognate nucleotide on either of the two binding partner oligonucleotides, thus forming a gap positioned between the binding partner oligonucleotides. The length of the gap is determined by the number of nucleotides on the bridging oligonucleotide between the two binding partner oligonucleotides that have no cognate nucleotides on either binding partner oligonucleotide. Thus, if only a single nucleotide of the bridging oligonucleotide situated between the two binding partner oligonucleotides has no cognate nucleotide on either binding partner oligonucleotide, the gap between the binding partner oligonucleotides is one nucleotide in length. The gap may be of any length (as measured by the number of nucleotides of the bridging oligonucleotide positioned between the binding partner oligonucleotides that have no cognate nucleotides) so long as each binding partner is able to anneal to the bridging oligonucleotide with enough strength to prevent dissociation. Similarly, the position of the gap may be located at any point along the length of the bridging oligonucleotide, so long as each binding partner is able to anneal to the bridging oligonucleotide with enough strength to prevent dissociation. One embodiment of gapped ladder assembly is depicted in FIG. 1B.

Generation of Sequence Diversity in the Ladder Complex

In certain embodiments of the present invention, sequence diversity may be generated in the ladder complex by substituting one or more alternative oligonucleotides for one of the oligonucleotides that comprises the ladder complex. In certain of these embodiments, the alternative oligonucleotides differ from the original oligonucleotide at one or more nucleotide positions. For example, if one of the oligonucleotides of the ladder complex contains an adenine base at position x, three alternative oligonucleotides that contain cytidine, guanine or thymine at position x may be produced, resulting in four alternative variations of the ladder complex. If two nucleotides are altered in a particular oligonucleotide, sixteen variations of the ladder complex may be generated, and so on. Additionally or alternatively, the alternative oligonucleotides of the ladder complex may differ from each other in that they contain one or more deletions, insertions or rearrangements, so long as the oligonucleotides are still able to form a ladder complex. In certain embodiments, the utilization of alternative oligonucleotides containing one or more deletions, insertions or rearrangements will result in a new ladder complex in which one or more of the original oligonucleotides of original new ladder complex are excluded.

In some embodiments, the ladder complex comprises a sequence that encodes a polypeptide or a portion of a polypeptide. Thus, altering of the nucleotide sequence of the ladder complex will result in a ladder complex that may encode a variation of the polypeptide or portion comprising an alternative amino acid sequence. Polypeptides have become increasingly important therapeutic, agricultural and commercial agents. More and more discovery and research is directed towards the identification of polypeptides that function as useful agents or that are themselves targets of a drug molecule. Often, a small change in the amino acid sequence of a polypeptide of interest can have a dramatic effect on its properties. Alternatively or additionally, the addition, deletion or modification of a particular structural domain of a polypeptide may also affect its properties in dramatic and unanticipated ways. Identifying those particular amino acid sequences and structural domains and optimizing them to generate a polypeptide with one or more desired properties is a critical challenge in the development of new and useful variants of known polypeptide sequences. With the advent of large-scale sequencing projects, an overwhelming number of genes predicted to encode one or more polypeptides are now known. Even with this extensive knowledge of predicted polypeptide sequence data, researchers are often hampered in their efforts to develop therapeutically, agriculturally or commercially useful variants of these polypeptides by a lack of functional knowledge about these predicted polypeptides and their domains.

Due to degeneracy of the genetic code, an alteration in the nucleotide sequence of the ladder complex may result in a so-called "silent substitution" that does not alter the peptide sequence of the polypeptide or portion that it encodes. For example, the amino acid leucine is encoded by the codons CTT, CTC, CTG, and CTA. In this case, alteration of nucleotide located at the third position of a codon that encodes leucine would result in no change in the amino acid sequence of the polypeptide or portion encoded by the ladder complex.

The degeneracy of the genetic code simplifies the process of saturation mutagenesis of a polypeptide of interest. Saturation mutagenesis is achieved by comprehensively altering the sequence of a polypeptide at one or more amino acid positions such that a plurality of polypeptides that represents every possible amino acid substitution at that position(s) is generated. This technique permits an unbiased identification of the role that amino acid(s) plays in the function of the polypeptide and permits determination of which amino acid substitutions result in increased or decreased functionality of that polypeptide.

An amino acid is encoded by a codon, which consists of three consecutive nucleotides. Thus, there are sixty-four possible nucleotide combinations that may encode an amino acid. However, since many nucleotide substitutions in a given codon are silent and do not alter the amino acid sequence that codon encodes, not each of the sixty-four possible different codons need be generated to achieve saturation mutagenesis at a particular codon position. According to the present invention, to achieve saturation mutagenesis at a particular codon position of a ladder complex such that all twenty naturally occurring amino acids are represented, only twenty alternative oligonucleotides need be generated.

In certain embodiments, the ladder complex comprises one or more oligonucleotides that contain at least one degenerate nucleotide, represented by the letter "N". If the oligonucleotide encodes a polypeptide or portion of a polypeptide, the degenerate nucleotide sequence NNN at a particular codon position will generate a population of polypeptides or portions such that every possible amino acid at that position is represented in the population (note that the completely degenerate codon NNN will also generate truncated polypeptides or portions since three of the possible sixty-four nucleotide combinations encode stop codons). The degeneracy of the genetic code permits saturation mutagenesis of a particular amino acid by using fewer than the maximum sixty-four possible degenerate nucleotide combinations. For example, the degenerate nucleotide sequence NNG/T (where the first two positions of the codon are completely degenerate and the third position comprises either a guanine or thymine residue) will also generate a population of polypeptides or portions such that every possible amino acid at that codon position is represented in the polypeptides of the population. This reduces the number of degenerate oligonucleotides required to saturate a particular codon position from sixty-four to thirty-two. In accordance with teachings of the present invention, the practitioner may choose to use even fewer than the thirty-two degenerate oligonucleotides if he or she wishes to limit the possible amino acid alterations in the polypeptide sequences in the population.

Since almost all of the twenty naturally occurring amino acids are encoded by at least two codons, the practitioner has some discretion over which particular codon(s) to employ. For instance, certain organisms prefer one particular codon that encodes a given amino acid to another codon that encodes the same amino acid. In some embodiments, the nucleotide sequence of the ladder complex is propagated in a host cell in vivo (see Propagation of Inserted Chunk section, infra). In certain aspects of these embodiments, the practitioner may choose to use a codon preferred by that host cell over another codon that encodes that same amino acid for purposes of robust propagation. Similarly, a particular codon might render the oligonucleotide partly self-complementary or otherwise affect its ability to form the ladder complex. In this case, the practitioner may choose another codon that encodes the same amino acid to alleviate the problem.

Methods of the present invention are particularly suited to generating diversity in a particular polypeptide of interest. By altering the nucleotide sequence of a ladder complex that encodes a polypeptide, it is possible to engineer a practically limitless number of polypeptide variants that can be tested for whatever quality the practitioner deems important. For example, a polypeptide that is part of a family of two or more homologous polypeptides may be altered to generate a chimeric polypeptide comprising polypeptide sequences or domains from two or more members of the family. By choosing appropriate oligonucleotides to form the ladder complex, the practitioner will be able to quickly and easily "swap" in particular sequences or domains from other members of the family. Thus, if the family consists of two polypeptide members, each of which contains three domains of interest, methods of the present invention enable generation of six chimeric polypeptides, each of which contains a different combination of the three domains of interest.

Similarly, by choosing appropriate alternate oligonucleotides to form the ladder complex, methods of the present invention enable the practitioner to "swap" in homologous domains from otherwise non-homologous polypeptides. Thus, to give but one example, a zinc finger domain from a transcription factor may be substituted with a zinc finger domain from a translational repressor protein and the chimeric polypeptide may be tested for its ability to activate transcription (or for any other property in which the practitioner is interested).

Methods of the present invention of introducing sequence diversity in a nucleotide sequence (that may optionally encode a polypeptide) offer a significant advantage over many other methods of generating diversity. For example, the method disclosed by Patten et al. (U.S. Pat. Nos. 6,579,678 and 6,613,514) utilizes random recombination of two or more parental nucleic acid molecules to generate diversity in a population of progeny nucleic acid molecules. After recombination, the progeny nucleic acid molecules may be chimeric and may contain sequence portions from two or more of the parental nucleic acid molecules. However, the method of Patten et al. suffers from the drawback that the recombination event is entirely random. Thus, there is no guarantee that a particular progeny nucleic acid molecule containing a particular combination of parental regions will be produced. Additionally, since the recombination is random, one or more of the parental nucleic acid molecules may fail to undergo recombination or may be reconstituted in the recombination reaction. Methods of the present invention allow the practitioner to avoid these disadvantages by allowing him or her to specifically engineer a nucleotide sequence by choosing or generating appropriate oligonucleotides of the ladder complex. Thus, the practitioner has complete control of the ladder complex sequence and need not rely on stochastic processes in the hope of generating a desired nucleotide sequence.

Furthermore, the method disclosed by Patten et al. requires substantial screening of the population of progeny polynucleotides to determine which chimeric progeny nucleic acid molecules contain a desired combination of parental sequences and to filter out any unwanted non-recombined or reconstituted parental nucleic acid molecules. Methods of the present invention allow the practitioner to avoid the screening step of Patten et al. Since the practitioner is able to generate a specific desired nucleotide sequence by choosing or generating appropriate oligonucleotides of the ladder complex, it is not inherently necessary to screen for unwanted artifacts generated by the recombination process.

In certain embodiments, the ladder complex comprises a sequence that comprises a regulatory element that regulates a polypeptide of interest. For example, the sequence may comprise a promoter element. By choosing appropriate alternate oligonucleotides to form the ladder complex, alternate versions of the promoter sequence can be generated. Using teachings of the present invention, it is possible to introduce these alternate forms of the promoter into, for example, an expression vector that contains a reporter gene such that the alternate forms of the promoter regulate expression of the reporter gene. By measuring the levels and/or activity of the reporter gene, it is possible to determine which nucleic acid residues are important for the expression of a polypeptide under control of that promoter and which nucleotide substitutions result in greater or lesser expression of that reporter gene. Methods of the present invention are suitable for generating alternate versions of any promoter element. A wide variety of promoter elements are known, including but not limited to constitutive elements, inducible elements and tissue-specific elements. One of ordinary skill in the art will be able to determine which promoter element or elements he or she wishes to alter. Furthermore, one of ordinary skill in the art will be able to determine which alterations to make to those promoter elements. In certain embodiments, one or more nucleotides of the promoter element are subjected to saturation mutagenesis such that every possible sequence combination of those nucleotides is generated.

In some embodiments, the ladder complex comprises a sequence that comprises a sequence that encodes a polypeptide that optionally contains one or more intron sequences. In some embodiments, methods of the present invention may be used to introduce one or more introns into the ladder complex sequence. Additionally or alternatively, methods of the present invention may be used to remove one or more introns from the ladder complex sequence. In some embodiments, methods of the present invention may additionally or alternatively be used to introduce additional sequence elements or nucleotides into one or more introns contained in the ladder complex sequence. In certain embodiments, methods of the present invention may additionally or alternatively be used to remove particular sequence elements or nucleotides from one or more introns contained in the ladder complex sequence. In some embodiments, methods of the present invention may additionally or alternatively be used to alter one or more splice sites of one or more introns contained in the ladder complex sequence. One of ordinary skill in the art will be able to determine which intron element or elements he or she wishes to introduce or alter. Furthermore, one of ordinary skill in the art will be able to determine which alterations to make to those intron elements. In certain embodiments, one or more nucleotides of the intron element are subjected to saturation mutagenesis such that every possible sequence combination of those nucleotides is generated.

In some embodiments, the ladder complex comprises a sequence that comprises a regulatory element that regulates the polypeptide of interest post-transcriptionally. For example, the ladder complex sequence may comprise a 5' or 3' UTR of a particular mRNA. Methods of the present invention may be used to introduce a regulatory element into the 5' or 3' UTR. Additionally or alternatively, methods of the present invention may be used to alter a regulatory element already present. As non-limiting examples, the regulatory element may regulate the stability or translation of that mRNA. One of ordinary skill in the art will be able to determine which UTR element or elements he or she wishes to introduce or alter. Furthermore, one of ordinary skill in the art will be able to determine which alterations to make to those UTR elements. In certain embodiments, one or more nucleotides of the UTR element are subjected to saturation mutagenesis such that every possible sequence combination of those nucleotides is generated.

Numerous other possible regulatory elements are known in the art and one of ordinary skill in the art will be able to choose which regulatory elements to alter and how to alter them according to teachings of the present invention.

Generation of Sequence Diversity in a Seamless Ladder

In a seamless ladder, no gap exists between adjacent oligonucleotides of the same strand. Thus, only the terminal oligonucleotides of a seamless ladder may optionally contain a single stranded portion. For example, in a ladder complex comprising a first terminal oligonucleotide, a second terminal oligonucleotide and at least two bridging oligonucleotides, one or both terminal oligonucleotides may contain a single stranded portion that is located distal to the last bridging oligonucleotide of the complementary strand to which the terminal oligonucleotide anneals.

Figure 4A:
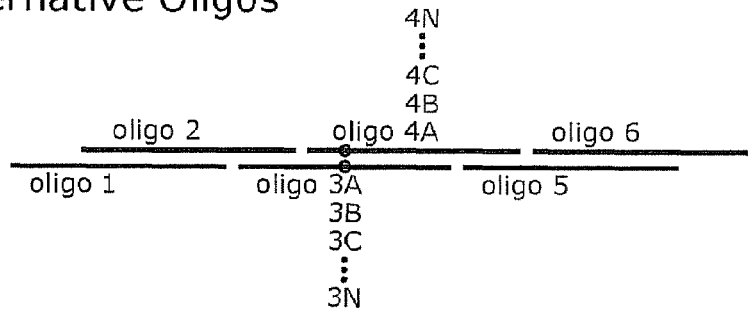
FIG. 4A shows a seamless ladder composed of six oligonucleotides, but any number of oligonucleotides may be annealed to form the ladder according to the present invention. Oligonucleotides 3 and 4 are provided as multiple alternative forms that differ from each other at one or more nucleotide positions, represented by the closed circles. The multiple oligonucleotide variants may be annealed in a pooled reaction (FIG. 4B). Alternatively, the multiple oligonucleotide variants may be annealed in individual reactions (FIG. 4C).

In certain embodiments, diversity in a seamless ladder may be generated by altering a nucleotide located in a bridging oligonucleotide (for example, see FIG. 4A). In some aspects of these embodiments, the cognate nucleotide in the binding partner oligonucleotide to which the altered nucleotide of the bridging oligonucleotide hybridizes is also altered such that it is complementary to the altered nucleotide of the bridging oligonucleotide. According to these aspects, the altered nucleotide in the bridging oligonucleotide will anneal to the altered complementary nucleotide of the binding partner oligonucleotide. In some aspects of these embodiments, a nucleotide located in a bridging oligonucleotide is altered, but the cognate nucleotide in its binding partner oligonucleotide is not altered. According to these aspects, the altered nucleotide in the ladder complex is no longer complementary to its cognate nucleotide on the binding partner oligonucleotide and will not anneal to it, thus forming a bubble at that position. If this ladder complex is subjected to a polymerase-mediated extension reaction to form a chunk (see Chunk Generation section, infra), two separate chunks will be generated, one chunk comprising a sequence containing the altered nucleotide of the bridging oligonucleotide and one chunk comprising a sequence containing the non-altered cognate nucleotide of the binding partner oligonucleotide.

Figure 6A:
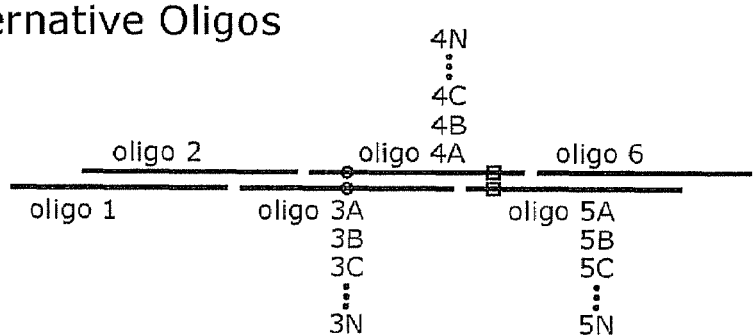
FIG. 6A shows a seamless oligonucleotide ladder that is altered at two positions. Oligonucleotides 3, 4 and 5 are provided as multiple alternative forms that differ from each other at one or more nucleotide positions, represented by the closed circles and closed squares. Although
Figure 6B:
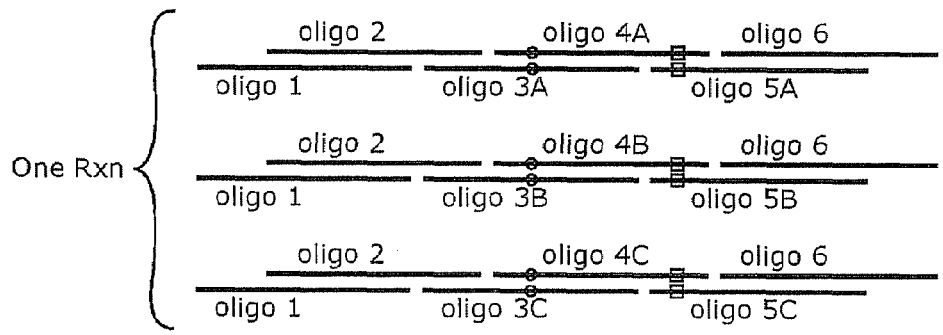
FIG. 6 shows one embodiment of generating diversity in a seamless oligonucleotide ladder in which multiple nucleotide positions are altered in the same reaction.
Figure 6C:
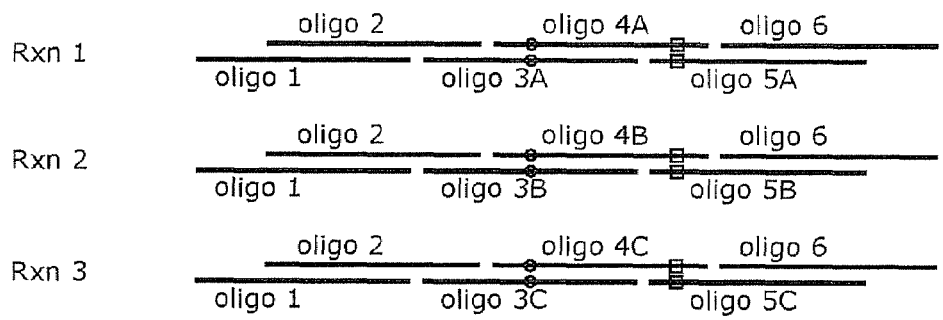

In certain embodiments, two or more nucleotides of a single bridging oligonucleotide may be altered simultaneously (for example, see FIG. 6). In some aspects of these embodiments, one binding partner oligonucleotide may contain all the cognate nucleotides of the nucleotides altered in the bridging oligonucleotide. In some aspects of these embodiments, at least one of the two or more nucleotides that are altered in the bridging oligonucleotide is cognate to a nucleotide on each of the two binding partner oligonucleotides. For example, FIG. 6 shows simultaneous alteration of two nucleotides, one of which is cognate to a nucleotide on one of the binding partner oligonucleotides, while the other is cognate to a nucleotide on the other binding partner oligonucleotide. The cognate nucleotides on the binding partner oligonucleotides may optionally be altered to comprise nucleotides complementary to the altered nucleotides of the bridging oligonucleotide, forming a ladder complex that lacks bubbles. Alternatively, the cognate nucleotides on the binding partner oligonucleotides may be left unaltered, forming a ladder complex that contains one or more bubbles.

In certain embodiments, two or more nucleotides located on separate bridging oligonucleotides may be altered simultaneously. The nucleotides of the binding partner oligonucleotides, which are cognate to the altered nucleotides of the separate bridging oligonucleotides, may optionally be altered to comprise nucleotides complementary to the altered nucleotides of the bridging oligonucleotides.

In certain embodiments, one or more nucleotides located in the single stranded portion of a terminal oligonucleotide may be altered. According to these embodiments, there are no cognate nucleotides located on another oligonucleotide that anneal to the altered nucleotides. In certain embodiments, one or more nucleotides located in the single stranded portions of both terminal oligonucleotides may be altered. In certain embodiments, one or more nucleotides located in the single stranded portion of a terminal oligonucleotide may be altered simultaneously with one or more nucleotides located in the portion of the terminal oligonucleotide that anneals to a binding partner oligonucleotide. The nucleotide(s) of the binding partner oligonucleotide that are cognate to the altered nucleotide(s) of the terminal oligonucleotide may optionally be altered to comprise nucleotides complementary to the altered nucleotides of the terminal oligonucleotide.

Figure 4B:
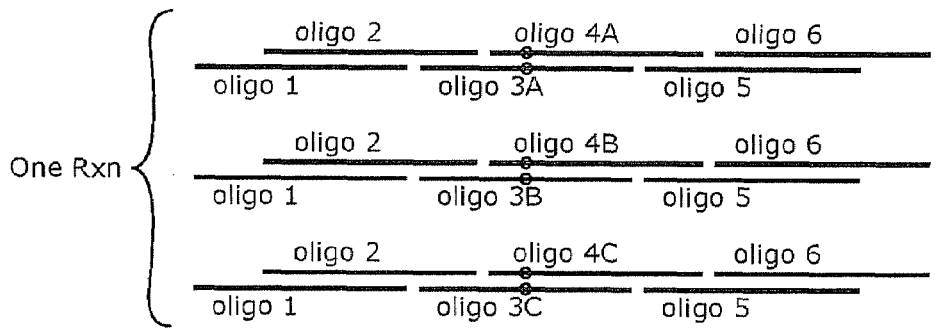
FIG. 4 shows certain embodiments of generating diversity in a seamless oligonucleotide ladder.
Figure 4C:
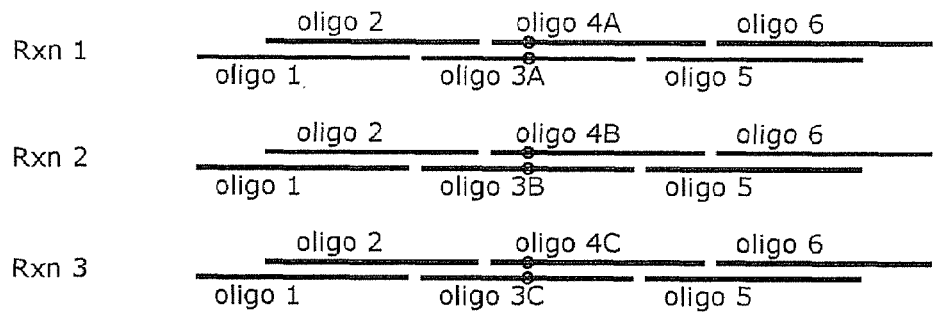

In certain embodiments, the oligonucleotides containing the altered nucleotides are pooled together and annealed in a single reaction (for example, see FIG. 4B). In other embodiments, the oligonucleotides containing the altered nucleotides are annealed in individual reactions (for example, see FIG. 4C).

Generation of Diversity in a Gapped Ladder

Figure 5A:
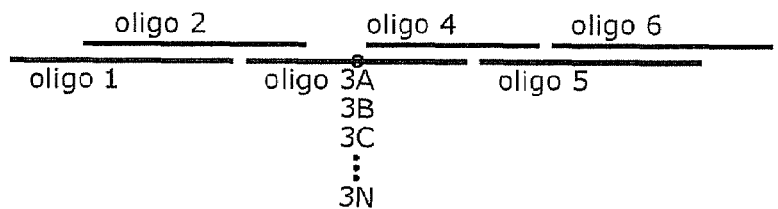
FIG. 5A shows a gapped ladder composed of six oligonucleotides, but any number of oligonucleotides may be annealed to form the ladder according to the present invention. Oligonucleotide 3 is provided as multiple alternative forms of the same sequence that differ from each other at one or more nucleotide positions, represented by the closed circles. The multiple oligonucleotide variants may be annealed in a pooled reaction (FIG. 5B). Alternatively, the multiple oligonucleotide variants may be annealed in individual reactions (FIG. 5C).

In certain embodiments, diversity in a gapped ladder may be generated by altering one or more nucleotides located in the single stranded portion of a bridging oligonucleotide located between the gap created by the two binding partner oligonucleotides (for example, see FIG. 5A). According to these embodiments, there are no cognate nucleotides to which the altered nucleotides may anneal, and thus only the sequence of the bridging oligonucleotide is altered. The altered nucleotides may be adjacent to each other or they may be separated from each other by one or more nucleotides.

In some embodiments, diversity is generated in a gapped ladder by altering one or more nucleotides located in the single stranded portion of a bridging oligonucleotide located between the gap created by the two binding partner oligonucleotides while simultaneously altering one or more nucleotides located in the one or both portions of the bridging oligonucleotide that anneal to one or both binding partner oligonucleotides. The cognate nucleotides of the binding partner oligonucleotide(s) may optionally be altered to comprise nucleotides complementary to the altered nucleotides of the bridging oligonucleotide, resulting in a gapped ladder complex that contains no bubbles. Alternatively, the cognate nucleotides of the binding partner oligonucleotide(s) may be left unaltered, resulting in a gapped ladder complex that contains one or more bubbles.

Figure 5B:
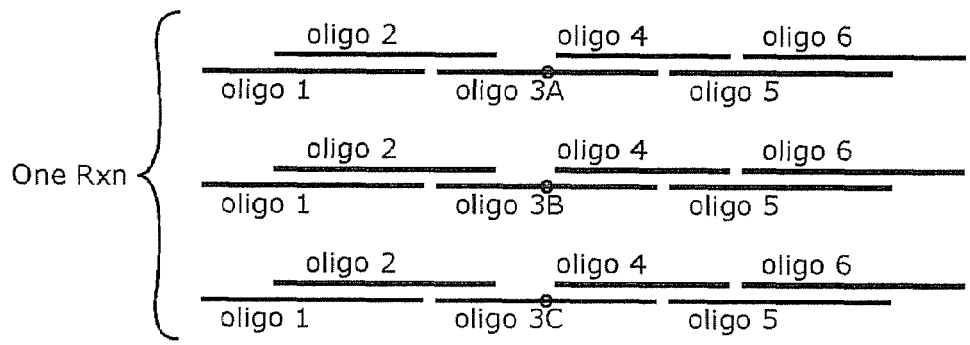
FIG. 5 shows certain embodiments of generating diversity in a gapped oligonucleotide ladder.
Figure 5C:
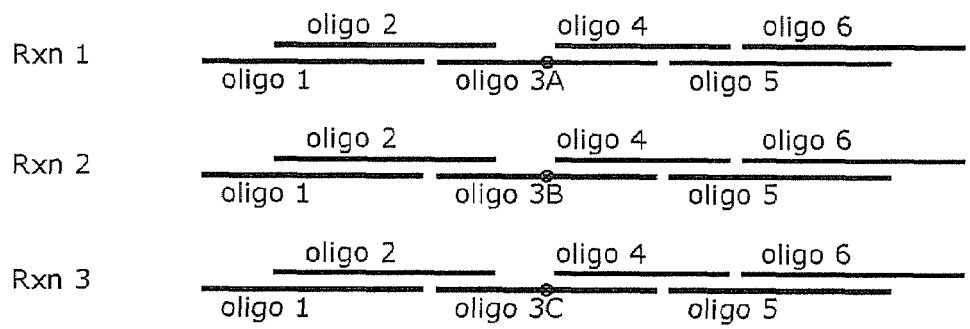

In certain embodiments, the oligonucleotides containing the altered nucleotides are pooled together and annealed in a single reaction (for example, see FIG. 5B). In some embodiments, the oligonucleotides containing the altered nucleotides are annealed in individual reactions (for example, see FIG. 5C).

Chunk Generation

In certain embodiments of the present invention, after generation of the ladder complex, two primers are provided and the ladder complex is subjected to a polymerase-mediated extension reaction. The resulting double stranded nucleic acid molecule is termed a "chunk". Depending on where the primers hybridize to the ladder complex and whether a portion of one or both of the primers extends beyond an end of the ladder complex, the chunk may be the longer, shorter or the same length as the ladder complex. For example, if both primers anneal to the ladder complex such that the ends of the primers are flush with the termini of the ladder complex, polymerase-mediated extension of the ladder complex will produce a chunk the same length as the ladder complex. Similarly, if one or both primers anneals to the ladder complex internally such that the ladder complex extends beyond the end of one or both primers, polymerase-mediated extension of the ladder complex will produce a chunk shorter than the length of the ladder complex. If each primer anneals to a terminus of the ladder complex such that at least a portion of at least one primer extends beyond that terminus of the ladder complex, polymerase-mediated extension of the ladder complex will produce a chunk longer than the length of the ladder complex.

In certain embodiments, at least one of the primers contains one or more terminator nucleotides and/or one or more terminator structures that do not serve as a template for the polymerase used in the polymerase-mediated extension reaction, such that the chunk generated from the extension reactions contains at least one 5' overhang.

Any polymerase that is able to copy at least one of the nucleotides present in the primers may be used in the polymerase-mediated extension of the ladder complex. In certain embodiments, the polymerase-mediated extension reaction used to extend the ladder complex is a polymerase chain reaction ("PCR"). In certain aspects of this embodiment, a thermostable polymerase may be used such that the ladder complex may be extended by PCR in one reaction chamber. As non-limiting examples, thermostable polymerases derived from *Thermus aquaticus* ("Taq"), *Pyrococcus furiousus* ("Pfu"), *Thermus thermophilus* ("Tth"), *Thermococcus gorgonarius* ("Tgo"), *Thermus flavus* ("Tfl"), *Thermus brocki-* anus ("Tbr"), *Thermococcus litoralis* ("Vent") and *Bacillus stearothermophilus* ("Bst") may be used. One of ordinary skill in the art will be aware of other appropriate polymerases that may be used in the polymerase-mediated extension, as well as the appropriate enzymatic conditions that facilitate and/or allow polymerization.

According to teachings of the present invention, a double stranded chunk may be generated from either a seamless or a gapped ladder complex. Neither the presence of one or more nicks in the strands comprising a seamless ladder complex, nor the presence of one or more gaps in the strands comprising a gapped ladder complex prevents the polymerase-mediated extension of that ladder complex. This phenomenon is useful since it eliminates the necessity of ligating the oligonucleotides comprising the ladder complex prior to the polymerase-mediated extension reaction. Furthermore, this phenomenon greatly facilitates the generation of diversity in a gapped ladder complex, since only one oligonucleotide (namely, the oligonucleotide that contains a single stranded portion opposite the gap between its two partner binding oligonucleotides) need be altered in order to introduce sequence variation in the ladder complex. According to these embodiments, alternate versions of the oligonucleotide that are altered at one or more nucleotide positions in the single stranded portion opposite the gap between its two partner binding oligonucleotides are provided, generating a plurality of diverse ladder complexes. The plurality of diverse ladder complexes is then subjected to a polymerase-mediated extension reaction, generating a plurality of double stranded chunks.

In certain embodiments, the nucleotide sequence of the chunk may be transcribed and optionally translated in vitro. For example, the chunk may be engineered to contain a promoter sequence that permits an RNA polymerase that recognizes that promoter sequence to transcribe the sequence of the chunk into RNA. Non-limiting examples of useful RNA polymerases include T7 RNA polymerase, T3 RNA polymerase, and SP6 polymerase. One of ordinary skill in the art will be aware of other useful RNA polymerases that may be employed in an in vitro transcription reaction. Additionally or alternatively, in certain aspects of these embodiments, the nucleotide sequence of the chunk may encode a polypeptide. In these aspects, the nucleotide sequence of the chunk may be engineered to contain a translation start site that is recognized by appropriate translation machinery. Thus, the nucleotide sequence of the chunk may be transcribed in vitro and subjected to in vitro translation to generate the polypeptide encoded by the chunk. Commonly, in vitro translation is performed in cell-free extracts. Non-limiting examples of cell-free extract systems include extracts from rabbit reticulocytes, wheat germ and *Escherichia coli*. One of ordinary skill in the art will be aware of other cell-free extract systems and other methods used for routine in vitro translation. The in vitro synthesis of polypeptides has a variety of applications, including production of a polypeptide that is not subject to normal post-translation modification, protein folding studies, incorporation of modified or unnatural amino acids for functional studies, production of polypeptides that are toxic to a particular host cell or are insoluble in that host cell, and production of polypeptides that undergo proteolytic degradation by intracellular proteases.

Gap Amplification

In certain embodiments of the present invention, the generated double stranded chunk is inserted into a nucleic acid acceptor molecule. In some aspects of these embodiments, the nucleic acid acceptor molecule contains at least one end comprising an overhang that is at least partly complementary with one overhanging end of the chunk such that the chunk is inserted into the nucleic acid acceptor molecule at a single position and in a single orientation. The other end of the nucleic acid acceptor molecule may optionally contain an end comprising an overhang that is at least partly complementary with the other overhanging end of the chunk. Thus, according to teachings of the present invention, the practitioner is freed from the requirement of burdensome screening to determine the location and orientation of the insertion. In some embodiments, the ends of the nucleic acid acceptor molecule are not complementary with each other, such that intramolecular interactions between the ends of the nucleic acid acceptor molecule are minimized. In certain embodiments, the nucleic acid acceptor molecule is a vector that can be propagated in bacteria, yeast, cultured mammalian cells, cultured insect cells or any of a number of other cell types known to one of ordinary skill in the art.

The nucleic acid acceptor molecule may be prepared for chunk insertion by any of several known techniques in the art. For example, the nucleic acid acceptor molecule may be cleaved with appropriate restriction enzymes that leave at least one end that is at least partly complementary with one end of the chunk. Additionally or alternatively, the nucleic acid acceptor molecule may be generated by ligating two or more double stranded nucleic acid molecules together to form a single double stranded nucleic acid molecule that contains at least one end that is at least partly complementary with one end of the chunk.

In certain embodiments of the present invention, the nucleic acid acceptor molecule is prepared for chunk insertion in a process termed "Gap Amplification". Gap amplification comprises subjecting a template nucleic acid molecule to one or more polymerase-mediated extensions such that one or more linear nucleic acid acceptor molecules are generated. For example, primers may be annealed to a template nucleic acid molecule and extended against that template nucleic acid molecule to generate the nucleic acid acceptor molecule. Depending on where the primers anneal, a greater or lesser portion of the original template nucleic acid molecule may be retained in the resulting nucleic acid acceptor molecule. This method is extremely powerful since it allows the practitioner to determine exactly how much of the original template nucleic acid molecule will be retained in the generated nucleic acid acceptor molecule.

In certain embodiments, gap amplification is achieved by extending primers, one or both of which contain one or more terminator nucleotides and/or one or more terminator structures to generate a nucleic acid acceptor molecule that contains at least one 5' overhang that is at least partly complementary to one end of the chunk to be inserted. In certain embodiments, the polymerase-mediated extension reaction is PCR.

Figure 2A:
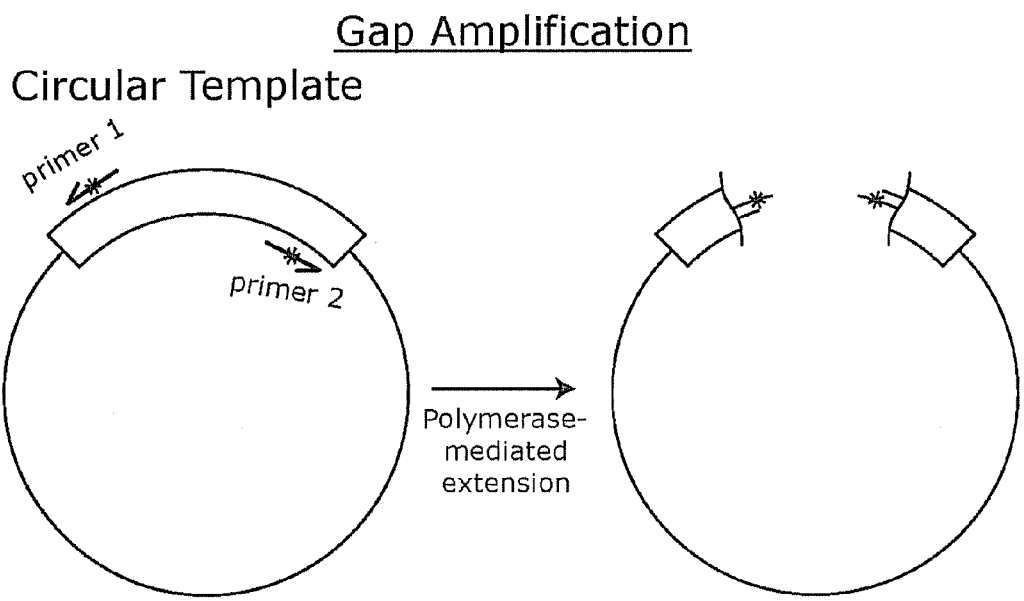
FIG. 2A shows an example of gap amplification of a circular template.

In some embodiments, the original template nucleic acid molecule is a circular vector that may optionally contain within it a sequence identical or similar to the sequence of the chunk (for example, see FIG. 2A). For example, the original circular vector may be an expression vector that contains a nucleotide sequence that encodes the polypeptide of interest under the control of a promoter. Alternatively, the original circular vector may be a cloning vector that simply contains the nucleotide sequence that encodes the polypeptide of interest. In certain aspects, primers are extended against this circular vector to generate a linear nucleic acid acceptor molecule that lacks a portion of the nucleotide sequence encoding the polypeptide. A double stranded chunk that contains a sequence identical or similar to the portion deleted from the nucleic acid acceptor molecule is then inserted into the nucleic acid acceptor molecule (see Chunk Insertion section, infra), reconstituting the original nucleotide sequence or a sequence similar to the original nucleotide sequence. Multiple chunks may be generated from a plurality of ladder complexes (see Generation of Sequence Diversity in the Ladder Complex section, supra), which, when inserted into the nucleic acid acceptor molecule, thereby generate a plurality of nucleotide sequences that encode a plurality of polypeptides.

Figure 2B:
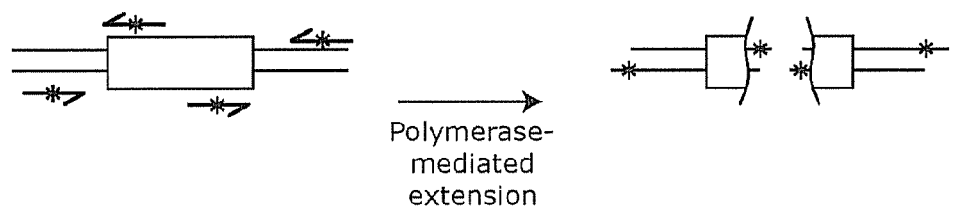
FIG. 2B shows an example of gap amplification of a linear template. The primers may be designed to contain one or more terminators that do not serve as a replication template for at least one polymerase (shown as asterisks). Amplifying the template nucleic acid molecule via a polymerase-mediated extension reaction using a polymerase that will not replicate the terminator(s) of the primer(s) results in a nucleic acid molecule that contains at least one 5' overhang beginning at the position of the terminator(s) in the primer(s).

In some embodiments, gap amplification is achieved by generating a nucleic acid acceptor molecule from a linear double stranded nucleic acid molecule (for example, see FIG. 2B). According to these embodiments, two sets of primers are used to generate two separate nucleic acid acceptor molecules. The first set of primers is used to generate a first nucleic acid acceptor molecule that contains an overhanging end that is at least partly complementary to one overhanging end of the chunk. The second set of primers is used to generate a second nucleic acid acceptor molecule that contains an overhanging end that is at least partly complementary to the other overhanging end of the chunk. According to these embodiments, the chunk is inserted between the first and second nucleic acid acceptor molecules (see Chunk Insertion section, infra).

Chunk Insertion

Figure 3:
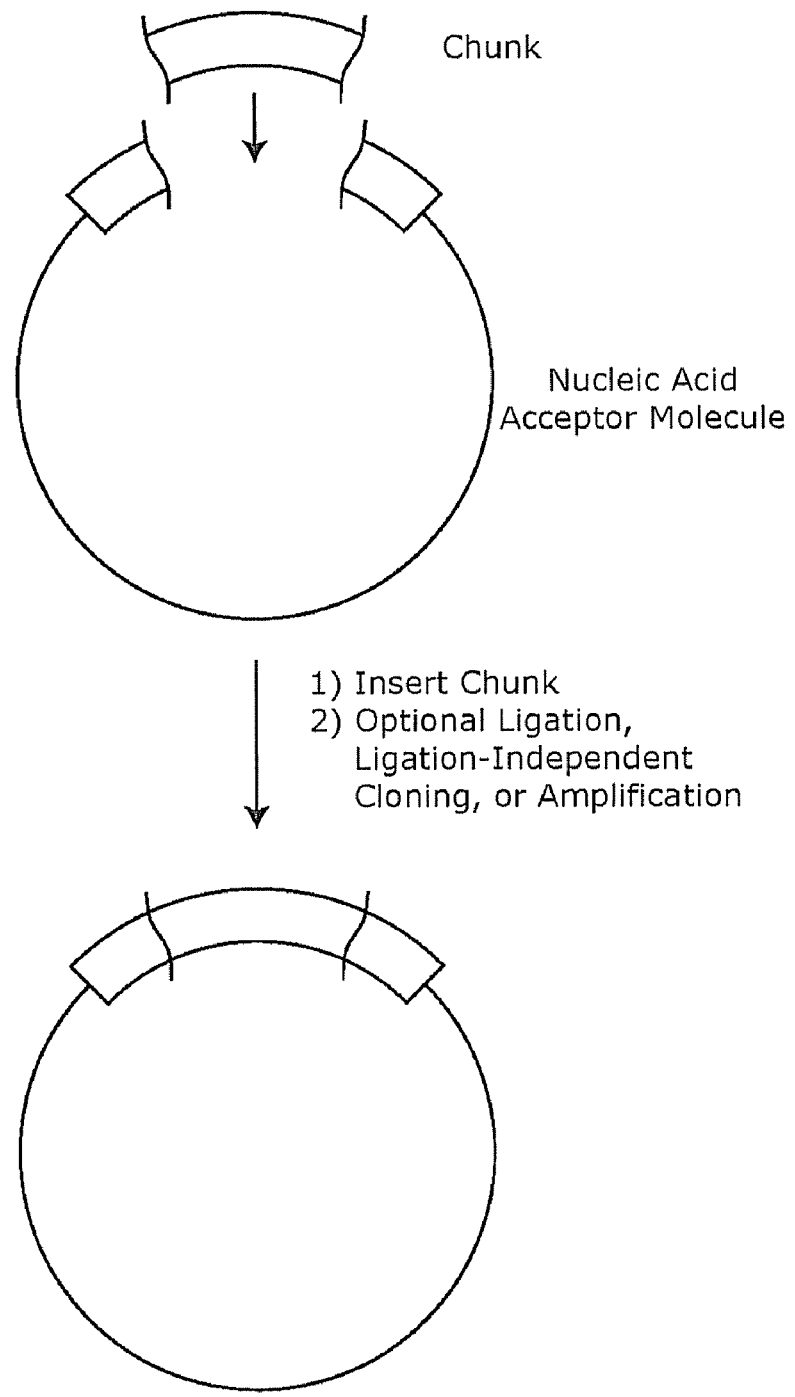
FIG. 3 shows one embodiment of Chunk Insertion. In this embodiment, a chunk with at least one overhang complementary to at least one overhang of a nucleic acid acceptor molecule is combined with the nucleic acid acceptor molecule, resulting in linkage of the chunk and the nucleic acid acceptor molecule. The chunk and the nucleic acid acceptor molecule may optionally be subjected to ligation, ligation-independent cloning, amplification, or any other method that results in linkage of the chunk with the nucleic acid acceptor molecule.

In certain embodiment, after generating a chunk and nucleic acid acceptor molecule, the chunk is then inserted into the nucleic acid acceptor molecule. In certain of the simplest embodiments, a single chunk is inserted into a single nucleic acid acceptor molecule (for example, see FIG. 3). According to some aspects of these embodiments, at least one of the ends of the nucleic acid acceptor molecule comprises an overhang that is at least partly complementary to one of the ends of the chunk, which also comprises an overhang, such that the chunk is inserted into the nucleic acid acceptor molecule at a single position and in a single orientation. The other end of the nucleic acid acceptor molecule may optionally contain an overhanging end that is at least partly complementary with the other end of the chunk that also comprises an overhang.

In certain embodiments, a plurality of chunks is generated from a plurality of ladder complexes. The plurality of chunks is then inserted into a nucleic acid acceptor molecule such that a plurality of resulting double stranded nucleic acid molecules is generated. In some aspects of these embodiments, the nucleic acid acceptor molecule has at least one end that comprises an overhang that is at least partly complementary to one overhanging end of each of member of the chunk plurality. According to these embodiment, the ends of the chunk molecules are not complementary with each other, such that only one chunk is inserted into a given nucleic acid acceptor molecule. In certain aspects of these embodiments, the plurality of chunks are pooled together and inserted into the nucleic acid acceptor molecule in one reaction. Since neither the ends of the plurality of chunks nor the ends of the nucleic acid acceptor molecule are complementary with one another, only one chunk is inserted into a given nucleic acid acceptor molecule. In certain aspects of these embodiments, each member of the plurality of chunks is inserted into the nucleic acid acceptor molecule in separate, individual reactions. Although more cumbersome at the front end, these embodiments have the advantage that only a single member of the plurality of chunks is present in each individual reaction, eliminating the necessity at the back end of subsequently isolating individual members of the plurality that have been inserted into the nucleic acid acceptor molecule.

In some embodiments, a single chunk is inserted into a plurality of ladder complexes. According to certain of these embodiments, each nucleic acid acceptor molecule contains at least one end comprising an overhang that is at least partly complementary to at least one overhanging end of the chunk to be inserted. In certain of these embodiments, the ends of the chunk molecule to be inserted are not complementary with each other, such that only one chunk is inserted into a single member of the nucleic acid acceptor molecule plurality. In some aspects of these embodiments, the plurality of nucleic acid acceptor molecules are pooled together and the chunk is inserted in one reaction. Since neither the ends of the plurality of nucleic acid molecules nor the ends of the chunk are complementary with one another, only one chunk is inserted into a given member of the nucleic acid acceptor molecule plurality. In some aspects of these embodiments, a chunk in inserted into each member of the plurality of nucleic acid molecules in separate, individual reactions.

Diversity Amplification

Figure 7A:
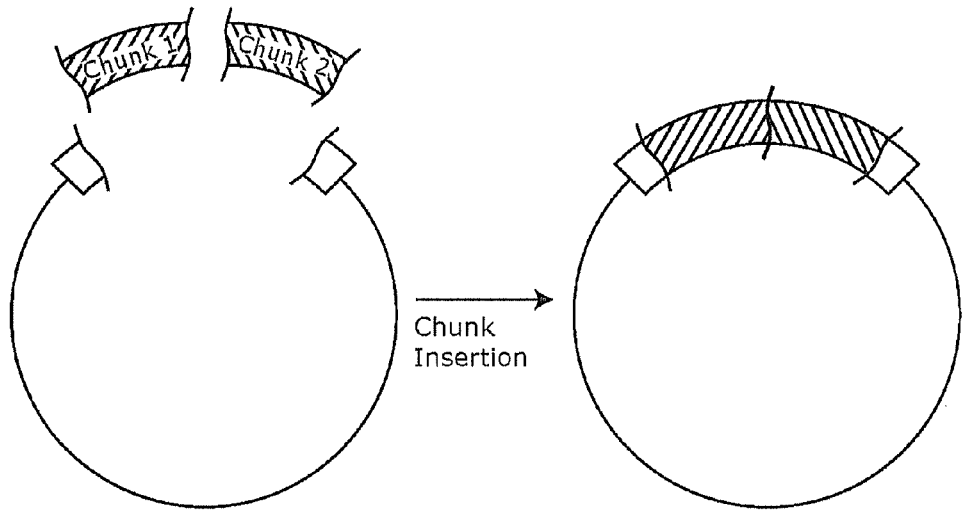
FIG. 7A shows an example of diversity amplification wherein the multiple chunks are inserted into a circular nucleic acid acceptor molecule at contiguous positions.

In certain embodiments, multiple alternative chunks are inserted into one or more nucleic acid acceptor molecules at one or more locations, a process termed "Diversity Amplification". In some embodiments of diversity amplification, the alternative chunks are inserted at contiguous locations in the nucleic acid acceptor molecule such that the alternative chunks are directly adjacent to each other in the resulting double stranded nucleic acid molecule (for example, see FIGS. 7A and 8A). In certain aspects of these embodiments, one end of a first chunk comprises an overhang that is at least partly complementary with one overhanging end of the nucleic acid acceptor molecule while the other end of the first chunk comprises another overhang that is at least partly complementary with an overhanging end of a second chunk that is inserted at a location contiguous to the first chunk. The other end of the second chunk may optionally comprise an overhang that is at least partly complementary to an overhanging end of a third chunk that is inserted at a location contiguous to the second chunk opposite the inserted first chunk. Alternatively, the other end of the second chunk may optionally comprise an overhang that is at least partly complementary to the other end of the nucleic acid acceptor molecule, which end also comprises an overhang.

Figure 7B:
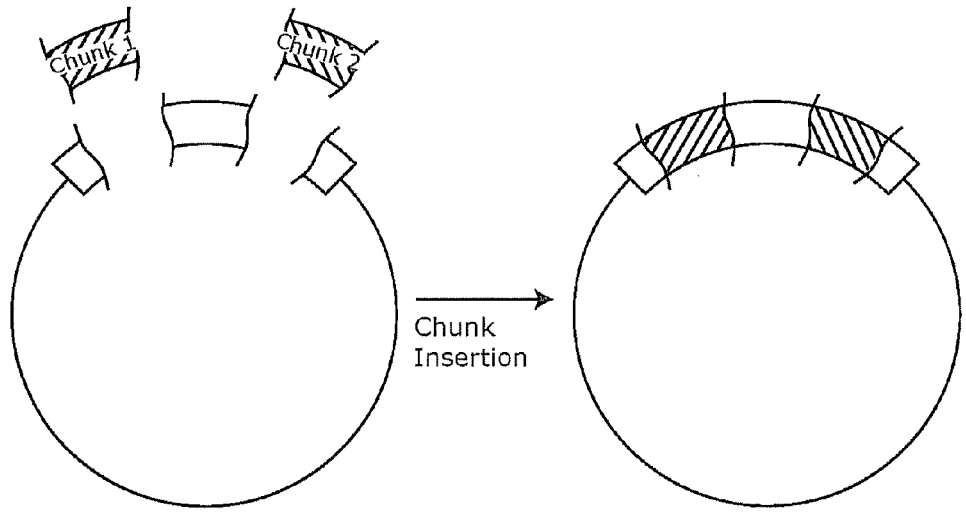
FIG. 7B shows an example of diversity amplification wherein the multiple chunks are inserted into a circular nucleic acid acceptor molecule at discrete positions.
Figure 8A:
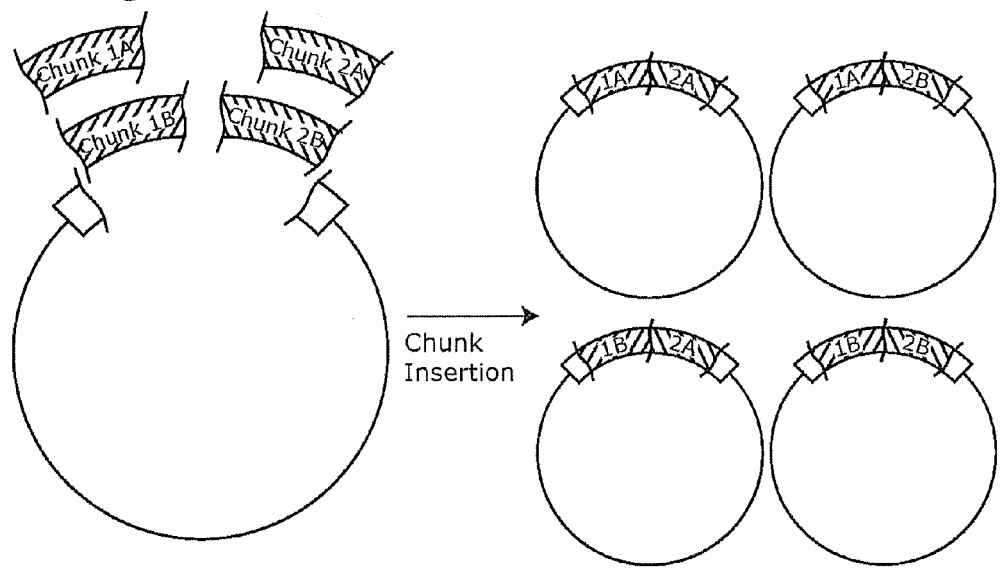
FIG. 8A shows an example of diversity amplification wherein the multiple chunks are inserted into a circular nucleic acid acceptor molecule at contiguous positions.
Figure 8B:
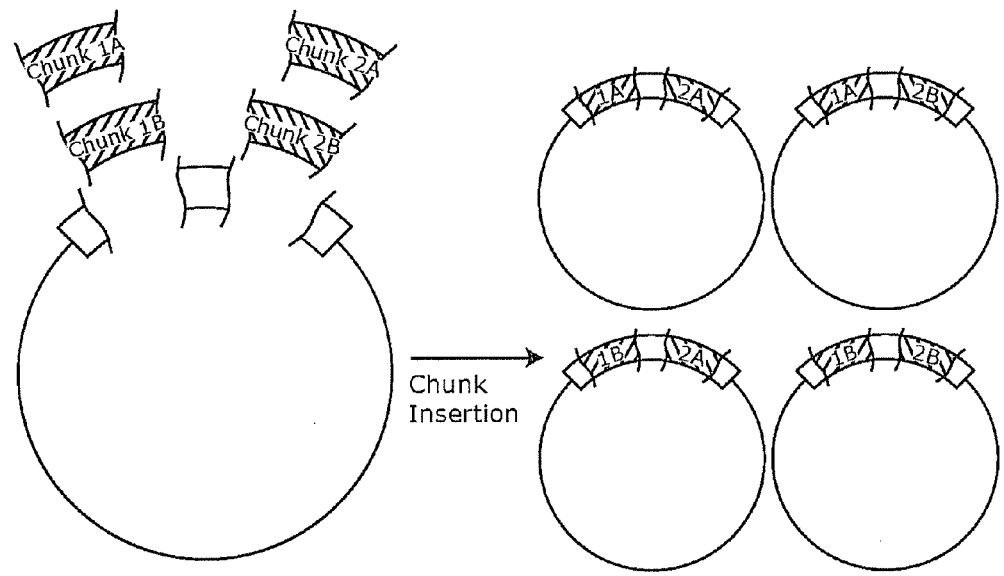
FIG. 8B shows an example of diversity amplification wherein the multiple chunks are inserted into a circular nucleic acid acceptor molecule at discrete positions. In these embodiments of diversity amplification, a related set of four nucleic acid molecules are generated. The nucleic acid molecules of the related set differ from each other in a pre-determined way at either one location (contiguous insertion, FIG. 8A) or at two locations (discrete insertion, FIG. 8B).

In some embodiments of diversity amplification, the alternative chunks are inserted at discrete locations in the nucleic acid acceptor molecule(s) such that the alternative chunks are not directly adjacent to each other in the resulting double stranded nucleic acid molecule (for example, see FIGS. 7B and 8B). According to these embodiments, at least one end of each of the chunks to be inserted comprises an overhang that is at least partly complementary to an overhanging end of the nucleic acid acceptor molecule. Furthermore, according to these embodiments, an intervening nucleic acid acceptor molecule that is located between each of any two given inserted chunks is provided.

Generation of nucleic acid molecules by diversity amplification may result in a related set of nucleic acid molecules that differ from each other at one or more pre-determined locations in pre-determined ways. For example, FIG. 8 shows two embodiments of diversity amplification two alternative chunks that can be inserted at each of two positions, resulting in a related set of four nucleic acid molecules. FIG. 8A shows an embodiment of contiguous insertion, while FIG. 8B shows an embodiment of discrete insertion. The four nucleic acid molecules that can be generated comprise a related set that differ from each other in four possible ways at either one location (contiguous insertion, FIG. 8A) or at two locations (discrete insertion, FIG. 8B). It will be understood by those of ordinary skill in the art that any number of alternative chunks may be inserted at any particular location, and that any number of locations can be employed to generate a related set of nucleic acid molecules.

In certain embodiments of diversity amplification, the alternative chunks are inserted simultaneously into the nucleic acid acceptor molecule. In certain embodiments of diversity amplification, the alternative chunks are inserted sequentially into the nucleic acid acceptor molecule. In some aspects of these embodiments, a first nucleic acid acceptor molecule is generated from a template nucleic acid molecule, for example by gap amplification. A chunk is then inserted into the first nucleic acid acceptor molecule. The resulting chunk/first nucleic acid acceptor molecule complex is then subjected to another round of gap amplification, producing a second nucleic acid acceptor molecule. Another chunk is then inserted into the second nucleic acid acceptor molecule. This process can be repeated ad infinitum to insert a potentially limitless number of chunks into an original nucleic acid acceptor molecule. In some aspects of these embodiments, all nucleic acid acceptor molecules are prepared prior to chunk insertion. The chunks are provided sequentially and the chunk/nucleic acid acceptor molecule complexes are not subjected to further rounds of gap amplification.

Diversity amplification provides a powerful method of generating a large amount of diversity in a nucleic acid sequence. For example, a nucleic acid sequence may be altered at two locations by the insertion of three alternative versions of a chunk, which differ from each other at one or more nucleotide positions. In this example, a related set of six different variants of the parent nucleic acid sequence may be generated. If three alternative chunks may be inserted in each of three locations in the nucleotide sequence, a set of nine different variants may be generated. Diversity amplification is particularly useful when one wishes to test the properties of a polypeptide that contains two or more domains or amino acid sequences of interest. By altering the nucleotide sequence of a ladder complex that contains a sequence encoding a polypeptide or portion of a polypeptide, the practitioner is able to quickly and easily generate specific variants of a polypeptide of interest. For example, diversity amplification allows one to test practically limitless variations of a given transcription factor of interest by generating alternate versions of the DNA binding domain, the transcriptional activation domain or any other domain of interest to the practitioner. One of ordinary skill in the art will be able to choose the number and type of altered versions of a given polypeptide to generate using methods disclosed herein, based on his or her experimental, commercial or other needs.

Propagation of Inserted Chunk

Once a chunk has been inserted into a nucleic acid acceptor molecule, the chunk may be propagated by any in vivo or in vitro method known in the art. For example, the inserted chunk may first be ligated in vitro to the nucleic acid acceptor molecule and subsequently introduced into a host cell that is capable of clonally propagating the ligated nucleic acid molecule.

In some embodiments, the chunk and nucleic acid acceptor molecule are not ligated in vitro prior to introduction into a host cell. According to these embodiments, once introduced, internal mechanisms of the host cell are sufficient to covalently link the chunk and nucleic acid acceptor molecule, thus forming a double stranded nucleic acid molecule that is then clonally propagated by the host cell. As discussed previously, one advantage of the present invention is that ligation of the annealed ladder complex is not necessary prior to generation of a chunk via a polymerase-mediated extension reaction. Thus, in certain embodiments of the present invention, in vitro ligation is not performed at any step during the process.

In certain embodiments, the chunk is propagated in vitro. For example, once a chunk has been inserted into a nucleic acid acceptor molecule, the chunk/nucleic acid acceptor molecule complex may be extended via a polymerase-mediated extension reaction. In certain embodiments, the polymerase-mediated extension reaction comprises PCR. By choosing a pair of primers that anneal to cognate nucleotides on separate strands of the chunk/nucleic acid acceptor molecule complex, it is possible to replicate the entire chunk/nucleic acid acceptor molecule complex without the loss of any base pairs. In some embodiments, the primers contain one or more nucleotides that are not copied by the polymerase utilized in the extension reaction, generating a linear double stranded nucleic acid molecule that contains a 5' overhang at each end. If the primers are chosen such that the generated 5' overhangs are at least partly complementary with each other, the ends of the resulting linear double stranded nucleic acid molecule may be annealed to form a circular double stranded nucleic acid molecule. In certain aspects of these embodiments, the resulting circular double stranded nucleic acid molecule is subjected to in vitro ligation to form a circular molecule that contains no nicks. In certain aspects of these embodiments, the resulting circular double stranded nucleic acid molecule is introduced into a host cell and further propagated as described above.

EXAMPLES

Example 1

Ladder Assembly

Strains, Plasmids, and Media: All genetic manipulations were carried out in XL-1 Blue chemically competent *E. coli* cells (Novagen, Madison, Wis.). A custom plasmid containing the colEI origin of replication, resistance genes for both ampicillin and kanamycin, and SacB gene (for negative selection of residual parental plasmid during transformation) at the segment insertion site was used as the cloning vector for all segments. Transformed cells were plated on LB agar supplemented with 5% sucrose and 100 µg/mL ampicillin. Resulting colonies were cultured in CircleGrow broth (Qbiogene, Carlsbad, Calif.) supplemented with ampicillin to a final concentration of 100 µg/mL.

PCR for Vector Preparation: Each 50 µl reaction consisted of 25 pMol of each primer, 1×Pfu Buffer (10 mM $(NH_4)_2SO_4$, 20 mM Tris (pH8.8), 2 mM $MgSO_4$, 10 mM KCl, 0.1% Triton X-100 and 1 mg/ml bovine serum albumin), 1 mM additional $MgSO_4$, 0.2 mM of each dNTP, 0.5 ng of plasmid template and 2.5 units each of cloned Pfu and Pfu Turbo polymerases (Stratagene, La Jolla, Calif.). Primers were purchased from Integrated DNA Technologies, Coralville, Iowa. Priming sites on the parental plasmid template flanked the SacB gene so that resulting PCR products would be SacB-. A typical step program for PCR was as follows: one cycle of 95° C., 5 minutes; 58-63° C., 3 minutes; 72° C., 7 minutes: followed by 30 cycles of 95° C., 45 seconds; 58-63° C., 45 seconds; 72° C., 5.25 minutes. PCR reactions were performed using a MJ Research gradient cycler. PCR efficiency was monitored by fractionating samples on a 0.75% agarose gel.

Ladder Assembly: Each 50 µl reaction consisted of 4.2 µg total of oligo ladders (consisting of a maximum of 16 overlapping 50-mer oligos at equal concentrations), 1×Pfu Buffer (10 mM $(NH_4)_2SO_4$, 20 mM Tris (pH8.8), 2 mM $MgSO_4$, 10 mM KCl, 0.1% Triton X-100 and 1 mg/ml bovine serum albumin), 2 mM additional $MgSO_4$, 0.2 mM of each dNTP, and 1.25 units each of cloned Pfu and Pfu Turbo polymerases (Stratagene, La Jolla, Calif.). DNA oligos were purchased from Integrated DNA Technologies, Coralville, Iowa. A typical step program for Ladder assembly was as follows: one cycle of 94° C., 1 minute; followed by 30 cycles of 94° C., 45 seconds; 55° C., 45 seconds; 72° C., 45 seconds. PCR reactions were performed using a MJ Research gradient cycler and the efficiency was monitored as above.

PCR for Joining Assembly Products/Cloning: Each 50 µl reaction consisted of 25 pMol of each primer, 1-3 ul of ladder assembly product template (consisting of a maximum of 3 overlapping segment precursors), 1×Pfu Buffer (10 mM $(NH_4)_2SO_4$, 20 mM Tris (pH8.8), 2 mM $MgSO_4$, 10 mM KCl, 0.1% Triton X-100 and 1 mg/ml bovine serum albumin), 1 mM additional $MgSO_4$, 0.2 mM of each dNTP, and 1.25 units each of cloned Pfu and Pfu Turbo polymerases (Stratagene, La Jolla, Calif.). Primers were purchased from Integrated DNA Technologies, Coralville, Iowa. A typical step program for PCR was as follows: one cycle of 95° C., 1-5 minutes; 58° C., 1 minute; 72° C., 1-3 minutes; followed by 30 cycles of 95° C., 45 seconds; 58° C., 45 seconds; 72° C., 45-90 seconds. PCR reactions were performed using a MJ Research gradient cycler and the efficiency was monitored as above.

PCR for Amplification of Sequence-verified Cloned Segments: Each 50 µl reaction consisted of 25 pMol of each primer, 1×Pfu Buffer (10 mM $(NH_4)_2SO_4$, 20 mM Tris (pH8.8), 2 mM $MgSO_4$, 10 mM KCl, 0.1% Triton X-100 and 1 mg/ml bovine serum albumin), 1 mM additional $MgSO_4$, 0.2 mM of each dNTP, 0.5 ng of plasmid template and 1.25 units each of cloned Pfu and Pfu Turbo polymerases (Stratagene, La Jolla, Calif.). Primers were purchased from Integrated DNA Technologies, Coralville, Iowa. A typical step program for PCR was as follows: one cycle of 95° C., 3-5 minutes; 50-60° C., 2 minutes; 72° C., 2-2.5 minutes/kb of sequence, followed by 30 cycles of 95° C., 45 seconds; 50-60° C., 45 seconds; 72° C., 1-1.5 minutes/kb of sequence. PCR reactions were performed using a MJ Research gradient cycler and the efficiency was monitored as above.

PCR for Joining Segments/Cloning: Each 50 µl reaction consisted of 25 pMol of each primer, 1-3 ul of segment templates (consisting of a maximum of 3 segments derived from either joining of assembly products or amplification of sequence-verified cloned segments and overlapping by at least 75 base pairs), 1×Pfu Buffer (10 mM $(NH_4)_2SO_4$, 20 mM Tris (pH8.8), 2 mM $MgSO_4$, 10 mM KCl, 0.1% Triton X-100 and 1 mg/ml bovine serum albumin), 1 mM additional $MgSO_4$, 0.2 mM of each dNTP, and 1.25 units each of cloned Pfu and Pfu Turbo polymerases (Stratagene, La Jolla, Calif.). Primers were purchased from Integrated DNA Technologies, Coralville, Iowa. A typical step program for PCR was as follows: one cycle of 95° C., 1-5 minutes; 58° C., 1 minute; 72° C., 2-2.5 minutes/kb of sequence, followed by 30 cycles of 95° C., 45 seconds; 58° C., 45 seconds; 72° C., 1-1.5 minutes/kb of sequence. PCR reactions were performed using a MJ Research gradient cycler and the efficiency was monitored as above.

DpnI digestion: PCR products were treated with DpnI restriction endonuclease (New England Biolabs, Beverly, Mass.) to preferentially digest parental plasmid DNA (when needed). Digestion was accomplished by combining 45 µL of each PCR reaction and 2 µL (10 units) of DpnI (New England Biolabs, Beverly, Mass.) and incubating for 2 hours at 37° C.

Annealing Reaction: For reactions involving the linkage of two DNA fragments (e.g., insertion of gene segment into custom vector), PCR reactions were concentrated using ethanol precipitation after DpnI treatment (when needed). Concentrated fragments were quantified by fluorescence spectrometry using the Picogreen reagent assay kit (Molecular Probes, Eugene, Oreg.) and Fluostar Optima Fluorometer/Spectrophotometer (BMG Labtechnologies, Durham, N.C.). A 10 µL annealing reaction was assembled with 100-200 ng of the larger PCR product, 3 molar equivalents of the smaller PCR product, and 1 µL of 10×DNA ligase buffer (660 mM Tris-HCl (pH7.6), 66 mM $MgCl_2$, 100 mM DTT, 660 µM ATP). The reaction was heated to 75° C. for 5 minutes and the reaction temperature was decreased 2° C. every 30 seconds until the approximate annealing temperature of the overhangs were reached. The reaction was held at this temperature for 15 minutes and then lowered by 2° C. every 30 seconds until a final reaction temperature of 36° C. was reached. Samples were centrifuged briefly and stored on ice until transformation.

Transformation: 5 µL of each annealing reaction was combined with 100 µL of XL-1 Blue chemically competent *E. coli* cells. After incubation on ice for 15 minutes, the reactions were subjected to a heat shock at 42° C. for 45 seconds. Following an additional incubation on ice for 2 minutes, 400 ul of SOC was added to each transformation. The transformations were incubated with shaking for 1 hour at 37° C. Aliquots were plated on LB agar supplemented with 5% sucrose and ampicillin to a final concentration of 100 µg/mL and incubated O/N at 37° C. Plasmid DNA was isolated from transformants and accurate ligation was verified by Sanger sequencing.

The foregoing description is to be understood as being representative only and is not intended to be limiting. Alternative methods and materials for implementing the invention and also additional applications will be apparent to one of skill in the art, and are intended to be included within the accompanying claims.

What is claimed is:

1. A method for generating a double stranded nucleic acid molecule comprising steps of:
   providing a collection of oligonucleotides comprising
     at least one first terminal oligonucleotide,
     at least one second terminal oligonucleotide, and
     at least two bridging oligonucleotides;
     wherein the first and second terminal oligonucleotides are characterized in that each terminal oligonucleotide anneals with only one other oligonucleotide in the collection and each bridging oligonucleotide is characterized in that each bridging oligonucleotide anneals with at least two other oligonucleotides in the collection;
   annealing the collection of oligonucleotides such that at least one ladder complex in generated, each such ladder complex comprising one first terminal oligonucleotide, one second terminal oligonucleotide and at least two bridging oligonucleotides such that the first terminal oligonucleotide and the second terminal oligonucleotide are connected to each other through at least two overlapping complementary bridging oligonucleotides, wherein there is no gap between oligonucleotides that are annealed to a bridging oligonucleotide;
   providing at least a first and a second primer, wherein at least one of the first or second primers includes at least one terminator nucleotide that does not serve as a template for at least one polymerase; and amplifying the ladder complex by polymerase-mediated extension of the first and second amplification primers such that the polymerase does not copy the terminator nucleotide and the extension reaction produces a product molecule containing at least a first overhang;

wherein the step of providing bridging oligonucleotides comprises providing at least a first and a second alternate bridging oligonucleotide, which first and second alternate bridging oligonucleotides are substantially similar to each other but differ from each other in at least a first variable nucleotide, which first variable nucleotide is located at the same relative position along the first and second alternate bridging oligonucleotides;

and wherein the step of providing bridging oligonucleotides further comprises providing at least a third and a fourth alternate bridging oligonucleotide, which third and fourth alternate bridging oligonucleotides are substantially similar to each other but differ from each other in at least a second variable nucleotide, which second variable nucleotide is located at the same relative position along the third and fourth alternate bridging oligonucleotides;

wherein the differing first variable nucleotide of the first alternate bridging oligonucleotide is complementary to the differing second variable nucleotide of the third alternate bridging oligonucleotide;

and wherein the differing first variable nucleotide of the second alternate bridging oligonucleotide is complementary to the differing second variable nucleotide of the fourth alternate bridging oligonucleotide.

2. The method of claim 1 further comprising:
providing at least one second double stranded nucleic acid acceptor molecule containing a second overhang, which second overhang is at least partly complementary to the first overhang; and
combining the first and second DNA molecules under conditions that allow hybridization of the first and second overhangs.

3. The method of claim 2, wherein the second double stranded DNA molecule is generated by extending a third and fourth primer in a polymerase-mediated extension reaction, at least one of the third or fourth primers including at least one nucleotide that is not copied by the polymerase employed in the extension reaction, such that a nucleic acid molecule having the second overhang is produced.

4. A method of generating a plurality of double stranded nucleic acid molecules comprising the steps of:
generating a collection of double stranded nucleic acid molecules, each of which is generated according to the method of claim 1, wherein the first overhang of each nucleic acid molecule of the collection is substantially similar;
providing at least one second double stranded DNA molecule containing a second overhang, which second overhang is at least partly complementary to the first overhang; and
combining the collection of double stranded DNA molecules and the second DNA molecules under conditions that allow hybridization of the first and second overhangs.

5. The method of claim 4, wherein the step of combining comprises combining individual double stranded molecules of the collection with the second double stranded DNA molecule in separate combination reactions.

6. The method of claim 4, wherein the step of combining comprises combining more than one double stranded molecule of the collection with the second double stranded DNA molecule simultaneously in a single combination reaction, such that only one double stranded molecule of the collection is combined with a single double stranded DNA molecule.

7. The method of claim 1, wherein a portion of each bridging oligonucleotide is exactly complementary to either the portion of the terminal oligonucleotide or to the portion of the other bridging oligonucleotide to which it anneals.

8. The method of claim 1, wherein a portion of each bridging oligonucleotide is exactly complementary to the portion of at least one other bridging oligonucleotide to which it anneals.

9. The method of claim 1, wherein the first and third alternate bridging oligonucleotides are provided in one amplification reaction, and the second and fourth alternate bridging oligonucleotides are provided in a different amplification reaction.

10. The method of claim 1, wherein the first, second, third and fourth alternate bridging oligonucleotides are provided simultaneously in the same amplification reaction.

11. The method of claim 1, wherein the step of providing bridging oligonucleotides comprises further providing at least a fifth and sixth alternate bridging oligonucleotide, which fifth and sixth alternate bridging oligonucleotides are substantially similar to each other but differ from each other in at least a third variable nucleotide, which third variable nucleotide is located at the same relative position along the fifth and sixth alternate bridging oligonucleotides;

wherein the third and fourth alternate bridging oligonucleotides further differ from each other in at least a fourth variable nucleotide, which fourth variable nucleotide is located at the same relative position along the third and fourth alternate bridging oligonucleotides and is located at a different position along the third and fourth alternate bridging oligonucleotides than the second variable nucleotide;

and wherein the differing third variable nucleotide of the fifth alternate bridging oligonucleotide is complementary to the differing fourth variable nucleotide of the third alternate bridging oligonucleotide;

and wherein the differing third variable nucleotide of the sixth alternate bridging oligonucleotide is complementary to the differing fourth variable nucleotide of the fourth alternate bridging oligonucleotide.

12. The method of claim 1, wherein the step of providing bridging oligonucleotides comprises further providing at least a fifth and sixth alternate bridging oligonucleotide, which fifth and sixth alternate bridging oligonucleotides are substantially similar to each other but differ from each other in at least a third variable nucleotide, which third variable nucleotide is located at the same relative position along the fifth and sixth alternate bridging oligonucleotides;

and wherein the step of providing bridging oligonucleotides further comprises providing at least a seventh and eighth alternate bridging oligonucleotide, which seventh and eighth alternate bridging oligonucleotides are substantially similar to each other but differ from each other in at least a fourth variable nucleotide, which fourth variable nucleotide is located at the same relative position along the seventh and eighth alternate bridging oligonucleotides;

wherein the differing third variable nucleotide of the fifth alternate bridging oligonucleotide is complementary to the differing fourth variable nucleotide of the seventh alternate bridging oligonucleotide;

and wherein the differing third variable nucleotide of the sixth alternate bridging oligonucleotide is complementary to the differing fourth variable nucleotide of the eighth alternate bridging oligonucleotide.

13. A method of generating a plurality of double stranded nucleic acid molecules comprising the steps of:
generating a collection of double stranded nucleic acid molecules, each of which is generated according to a method comprising,
providing a collection of oligonucleotides comprising
at least one first terminal oligonucleotide,
at least one second terminal oligonucleotide, and
at least two bridging oligonucleotides;
wherein the first and second terminal oligonucleotides are characterized in that each terminal oligonucleotide anneals with only one other oligonucleotide in the collection and each bridging oligonucleotide is characterized in that each bridging oligonucleotide anneals with at least two other oligonucleotides in the collection;
annealing the collection of oligonucleotides such that at least one ladder complex is generated, each such ladder complex comprising one first terminal oligonucleotide, one second terminal oligonucleotide and at least two bridging oligonucleotides such that the first terminal oligonucleotide and the second terminal oligonucleotide are connected to each other through at least two overlapping complementary bridging oligonucleotides, wherein the first terminal oligonucleotide and the second terminal oligonucleotide are positioned on separate strands at opposite ends of the ladder complex, and wherein in the step of annealing, at least one gap is created between the two oligonucleotides that are annealed to a given bridging oligonucleotide;
providing at least a first and a second primer, wherein at least one of the first or second primers includes at least one terminator nucleotide that does not serve as a template for at least one polvmerase; and
amplifying the ladder complex by polymerase-mediated extension of the first and second amplification primers such that the polymerase does not copy the terminator nucleotide and the extension reaction produces a product molecule containing at least a first overhang;
wherein the step of providing bridging oligonucleotides comprises providing at least two alternate bridging oligonucleotides, each alternate bridging oligonucleotide being substantially similar but differing from each other in at least one nucleotide located at the same relative position along the alternate bridging oligonucleotides, which position is located such that neither of the two oligonucleotides that anneal to the alternate bridging oligonucleotide and form said gap anneal with the alternate bridging oligonucleotide at said position.

14. The method of claim 13, wherein the separate alternate bridging oligonucleotides are each provided separately in different amplification reactions.

15. The method of claim 13, wherein more than one separate alternate bridging oligonucleotide is provided simultaneously in the same amplification reaction.

16. The method of claim 1, wherein at least one of the oligonucleotides of the ladder complex is approximately 25, 50,or 75nucleotides in length.

17. The method of claim 1 wherein the generated nucleic acid molecule encodes a polypeptide comprising a functional domain of a protein.

18. The method of claim 17, wherein the functional domain comprises a catalytic moiety.

19. A method of generating a plurality of double stranded nucleic acid molecules comprising the steps of:
generating a collection of double stranded nucleic acid molecules, each of which is generated according to the method of claim 13, wherein the first overhang of each nucleic acid molecule of the collection is substantially similar;
providing at least one second double stranded DNA molecule containing a second overhang, which second overhang is at least partly complementary to the first overhang; and
combining the collection of double stranded DNA molecules and the second DNA molecules under conditions that allow hybridization of the first and second overhangs.

20. The method of claim 19, wherein the step of combining comprises combining individual double stranded molecules of the collection with the second double stranded DNA molecule in separate combination reactions.

21. The method of claim 19, wherein the step of combining comprises combining more than one double stranded molecule of the collection with the second double stranded DNA molecule simultaneously in a single combination reaction, such that only one double stranded molecule of the collection is combined with a single double stranded DNA molecule.

22. The method of claim 13, wherein a portion of each bridging oligonucleotide is exactly complementary to either the portion of the terminal oligonucleotide or to the portion of the other bridging oligonucleotide to which it anneals.

23. The method of claim 13, wherein a portion of each bridging oligonucleotide is exactly complementary to the portion of at least one other bridging oligonucleotide to which it anneals.

24. The method of claim 13, wherein at least one of the oligonucleotides of the ladder complex is approximately 25, 50, or 75 nucleotides in length.

25. The method of claim 13, wherein the generated nucleic acid molecule encodes a polypeptide comprising a functional domain of a protein.

26. The method of claim 25, wherein the functional domain comprises a catalytic moiety.

27. The method of claim 13 wherein the gap spans approximately 1-5 nucleotides of the given bridging oligonucleotide.

* * * * *